US012780826B2

(12) United States Patent
Gray et al.

(10) Patent No.: US 12,780,826 B2
(45) Date of Patent: Nov. 3, 2026

(54) POTENT AND SELECTIVE INHIBITORS OF HER2

(71) Applicant: DANA-FARBER CANCER INSTITUTE, INC., Boston, MA (US)

(72) Inventors: Nathanael S. Gray, Boston, MA (US); John M. Hatcher, Boston, MA (US); Alyssa Verano, Boston, MA (US)

(73) Assignee: DANA-FARBER CANCER INSTITUTE, INC., Boston, MA (US)

( * ) Notice: Subject to any disclaimer, the term of this patent is extended or adjusted under 35 U.S.C. 154(b) by 669 days.

(21) Appl. No.: 18/044,462

(22) PCT Filed: Oct. 4, 2021

(86) PCT No.: PCT/US2021/053368

§ 371 (c)(1),
(2) Date: Mar. 8, 2023

(87) PCT Pub. No.: WO2022/076304

PCT Pub. Date: Apr. 14, 2022

(65) Prior Publication Data

US 2023/0295167 A1 Sep. 21, 2023

Related U.S. Application Data

(60) Provisional application No. 63/232,450, filed on Aug. 12, 2021, provisional application No. 63/087,517, filed on Oct. 5, 2020.

(51) Int. Cl.

| | |
|---|---|
| ***C07D 487/04*** | (2006.01) |
| ***A61P 35/00*** | (2006.01) |
| ***C07D 519/00*** | (2006.01) |

(52) U.S. Cl.

CPC ............ *C07D 487/04* (2013.01); *A61P 35/00* (2018.01); *C07D 519/00* (2013.01)

(58) Field of Classification Search

CPC ...... C07D 487/04; C07D 519/00; A61P 35/00
See application file for complete search history.

(56) References Cited

U.S. PATENT DOCUMENTS

| | | | |
|---|---|---|---|
| 8,343,961 | B2 | 1/2013 | Nicewonger |
| 9,101,622 | B2 | 8/2015 | Zeldis |
| 9,345,705 | B2 | 5/2016 | Shumway |
| 12,186,320 | B2 | 1/2025 | Irie |
| 2016/0045503 | A1 | 2/2016 | Goldstein et al. |
| 2017/0217970 | A1 | 8/2017 | Kawai et al. |
| 2019/0112312 | A1 | 4/2019 | Chen et al. |

FOREIGN PATENT DOCUMENTS

| | | | |
|---|---|---|---|
| CA | 2997051 A1 * | 3/2017 | .............. A61P 35/00 |
| EP | 3590516 | 1/2020 | |
| WO | 2013/010136 | 1/2013 | |
| WO | 2018/009544 | 1/2018 | |
| WO | 2019/214634 | 11/2019 | |
| WO | 2020/006265 | 1/2020 | |
| WO | WO 2021/175316 A1 | 9/2021 | |

OTHER PUBLICATIONS

Warmuth, M. et al. Ba/F3 cells and their use in kinase drug discovery. Curr Opin Oncol 2007, 19, 55-60. (Year: 2007).*
International Search Report and Written Opinion for International Application No. PCT/US2021/053368, mailed Feb. 16, 2022, 9 pages.
Shigematsu, H. et al., Somatic Mutations of the HER2 Kinase Domain in Lung Adenocarcinomas, Cancer Research, 2005, 1642-1646, 65(5).
Li, B. et al., Epidemiological study of HER-2 mutations among EGFR wild-type lung adenocarcinoma patients in China, BMC Cancer, 2016, 828, 16.
Slamon, D. J. et al., Human breast cancer: correlation of relapse and survival with amplification of the HER-2/neu oncogene, Science, 1987, 177-182, 235.
Slamon, D. J. et al., Studies of the HER-2/neu proto-oncogene in human breast and ovarian cancer, Science, 1989, 707-712, 244.
Tomizawa, K. et al., Prognostic and predictive implications of HER2/ERBB2/neu gene mutations in lung cancers, Lung Cancer, 2011, 139-144, 74.
Mazières, J. et al., Lung cancer that harbors an HER2 mutation: epidemiologic characteristics and therapeutic perspectives, Journal of Clinical Oncology, 2013, 1997-2003, 31(16).
Buttitta, F. et al., Mutational analysis of the HER2 gene in lung tumors from Caucasian patients: Mutations are mainly present in adenocarcinomas with bronchioloalveolar features, International Journal of Cancer, 2006, 2586-2591, 119.
Kris, M. G. et al., Using Multiplexed Assays of Oncogenic Drivers in Lung Cancers to Select Targeted Drugs, JAMA, 2014, 1998-2006, 311(19).

(Continued)

*Primary Examiner* — Jeffrey H Murray
*Assistant Examiner* — Kristen W Romero
(74) *Attorney, Agent, or Firm* — Nielsen IP Law LLC

(57) ABSTRACT

Disclosed are compounds and pharmaceutically acceptable salts and stereoisomers thereof that that are potent and selective inhibitors of HER2. Also disclosed are pharmaceutical compositions containing same, and methods of making and using the compounds to treat diseases and disorders associated with HER2.

8 Claims, No Drawings

(56) References Cited

OTHER PUBLICATIONS

De Grève, J. et al., Clinical activity of afatinib (BIBW 2992) in patients with lung adenocarcinoma with mutations in the kinase domain of HER2/neu, Lung Cancer, 2012, 123-127, 76.
Kris, M. G. et al., Targeting HER2 aberrations as actionable drivers in lung cancers: phase II trial of the pan-HER tyrosine kinase inhibitor dacomitinib in patients with HER2-mutant or amplified tumors, Annals of Oncology, 2015, 1421-1427, 26.
Mazières, J. et al., Lung cancer patients with HER2 mutations treated with chemotherapy and HER2-targeted drugs: results from the European EUHER2 cohort, Annals of Oncology, 2016, 281-286, 27.
Eng, J. et al., Outcomes of chemotherapies and HER2 directed therapies in advanced HER2-mutant lung cancers, Lung Cancer, 2016, 53-56, 99.
Gandhi, L. et al., Phase I Study of Neratinib in Combination With Temsirolimus in Patients With Human Epidermal Growth Factor Receptor 2-Dependent and Other Solid Tumors, Journal of Clinical Oncology, 2014, 68-75, 32(2).
Notice of Reasons for Rejection, JP Application No. 2023-521157, dated Aug. 12, 2025, 2 pages.
Irie, H. et al., TAS0728, A Covalent-binding, HER2-selective Kinase Inhibitor Shows Potent Antitumor Activity in Preclinical Models, Molecular Cancer Therapeutics, 2019, 733-742, 18 (4).
Moulder, S. L. et al., Phase I Study of ONT-380, a HER2 Inhibitor, in Patients with HER2+-Advanced Solid Tumors, with an Expansion Cohort in HER2+ Metastatic Breast Cancer (MBC), 2017, 3529-3536, 23(14).
Communication pursuant to Article 94(3) EPC, EP Application No. 21878296.9, dated May 28, 2025, 4 pages.
Communication extended European search report, EP Application No. 21878296.9, dated Nov. 18, 2024, 5 pages.
Office Action, CN Application No. 2021800813908, dated May 30, 2025, 4 pages.
Office Action, CN Application 2021800813908, dated Oct. 13, 2025, 3 pages.

* cited by examiner

POTENT AND SELECTIVE INHIBITORS OF HER2

RELATED APPLICATIONS

This application claims priority to U.S. Provisional Application No. 63/087,517 filed Oct. 5, 2020, and U.S. Provisional Application No. 63/232,450 filed Aug. 12, 2021, the entire content of which is hereby incorporated by reference in its entirety.

BACKGROUND

Mutations in the human epidermal growth factor receptor 2 (HER2, ERBB2) have been identified as oncogenic drivers. They occur in 2%-3% of non-small-cell lung cancer (NSCLC) (Shigematsu et al., Cancer Res., 65(5):1642-1646 (2005); Buttitta et al., Int. J. Cancer, 119(11):2586-2591 (2006); Tomizawa et al., Lung Cancer, 74(1):139-144 (2011); Mazieres et al., J. Clin. Oncol., 31(16):1997-2003 (2013)), and as high as 6.7% in EGFR/ALK/ROS1 triple-negative NSCLC (Li et al., BMC Cancer, 16(1):828 (2016)). In addition, amplification of the HER2 gene, overexpression of the HER2 protein, or both occur in approximately 15-25% of breast cancers, which are classified as HER2-positive (Slamon et al., Science, 235(4785):177-182 (1987); Slamon et al., Science, 244(4905):707-712 (1989)). HER2 mutations most commonly consist of exon 20 insertion mutants (Shigematsu et al., Cancer Res., 65(5):1642-1646 (2005)). The most frequent HER2 exon 20 insertion mutant consists of a 12-base pair in-frame insertion YVMA (p.A775_G776insYVMA), leading to downstream activation of the PI3'K-AKT and RAS-MAPK pathways (Tomizawa et al., Lung Cancer, 74(1):139-144 (2011)). Historically, patients with HER2-mutant NSCLC have a median overall survival (OS) of 1.6-1.9 years from the time of stage IV diagnosis (Kris et al., Jama-J. Am. Med. Assoc., 311(19): 1998-2006 (2014)). Several patient reports and series reporting on HER2-targeted agents in patients with HER2-mutant NSCLC, including afatinib, dacomitinib, neratinib and trastuzumab, have shown limited clinical activity (De Greve et al., Lung Cancer, 76(1):123-127 (2012); Kris et al., Ann. Oncol., 26(7):1421-1427 (2015); Gandhi et al., J. Clin. Onol., 32(2):68-75 (2014)); Mazieres et al., Ann. Oncol., 27(2):281-286 (2016)). Thus, chemotherapy remains the main strategy for this patient population (Eng et al., Lung Cancer, 99:53-56 (2016)).

Compounds possessing activity against HER2 mutations are needed, as they may have extended utility in treating tumors harboring such mutations.

SUMMARY

A first aspect of the present disclosure is directed to a compound represented by a structure of formula (I):

(I)

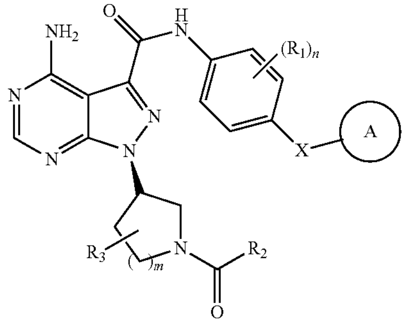

wherein $R_1$, $R_2$, $R_3$, X, m, n, and A are as defined herein, or a pharmaceutically acceptable salt or stereoisomer thereof.

Another aspect of the present disclosure is directed to a pharmaceutical composition that includes a therapeutically effective amount of a compound of formula (I) or a pharmaceutically acceptable salt or stereoisomer thereof, and a pharmaceutically acceptable carrier.

A further aspect of the present disclosure is directed to methods of treating a disease or disorder that is characterized or mediated by aberrant human epidermal growth factor receptor 2 (HER2) activity.

In some embodiments, the disease or disorder is cancer. In some embodiments, the cancer is breast cancer, ovarian cancer, gastrointestinal cancer, lung cancer, colon cancer, endometrial cancer, or thyroid cancer. In some embodiments, the cancer is non-small-cell lung cancer (NSCLC) or EGFR/ALK/ROS1 triple-negative NSCLC.

As demonstrated in the working examples, compounds of the present disclosure are potent and selective inhibitors of HER2.

DETAILED DESCRIPTION

Unless defined otherwise, all technical and scientific terms used herein have the same meaning as is commonly understood by one of skill in the art to which the subject matter herein belongs. As used in the specification and the appended claims, unless specified to the contrary, the following terms have the meaning indicated in order to facilitate the understanding of the present disclosure.

As used in the description and the appended claims, the singular forms "a", "an", and "the" include plural referents unless the context clearly dictates otherwise. Thus, for example, reference to "a composition" includes mixtures of two or more such compositions, reference to "an inhibitor" includes mixtures of two or more such inhibitors, and the like.

Unless stated otherwise, the term "about" means within 10% (e.g., within 5%, 2%, or 1%) of the particular value modified by the term "about."

The transitional term "comprising," which is synonymous with "including," "containing," or "characterized by," is inclusive or open-ended and does not exclude additional, unrecited elements or method steps. When used in the context of the number of heteroatoms in a heterocyclic structure, it means that the heterocyclic group that that minimum number of heteroatoms. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed compounds.

With respect to compounds disclosed herein, and to the extent the following terms are used herein to further describe them, the following definitions apply.

As used herein, the term "alkyl" refers to a saturated linear or branched-chain monovalent hydrocarbon radical. In one embodiment, the alkyl radical is a $C_1$-$C_{18}$ group. In other embodiments, the alkyl radical is a $C_0$-$C_6$, $C_0$-$C_5$, $C_0$-$C_3$, $C_1$-$C_{12}$, $C_1$-$C_6$, $C_1$-$C_5$, $C_1$-$C_4$ or $C_1$-$C_1$-$C_3$; group (wherein $C_0$ alkyl refers to a bond). Examples of alkyl groups include methyl, ethyl, 1-propyl, 2-propyl, i-propyl, 1-butyl, 2-methyl-1-propyl, 2-butyl, 2-methyl-2-propyl, 1-pentyl, n-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, heptyl, octyl, nonyl, decyl, undecyl and dodecyl. In some embodiments, an alkyl group is a $C_1$-$C_3$ alkyl group. In some embodiments, an alkyl group is a $C_1$-$C_2$ alkyl group, or a methyl group.

As used herein, the term "alkylene" refers to a straight or branched divalent hydrocarbon chain linking the rest of the molecule to a radical group, consisting solely of carbon and hydrogen, containing no unsaturation and having from one to 12 carbon atoms, for example, methylene, ethylene, propylene, n-butylene, and the like. The alkylene chain may be attached to the rest of the molecule through a single bond and to the radical group through a single bond. In some embodiments, the alkylene group contains one to 8 carbon atoms ($C_1$-$C_8$ alkylene). In other embodiments, an alkylene group contains one to 5 carbon atoms ($C_1$-$C_5$ alkylene). In other embodiments, an alkylene group contains one to 4 carbon atoms ($C_1$-$C_4$ alkylene). In other embodiments, an alkylene contains one to three carbon atoms ($C_1$-$C_3$ alkylene). In other embodiments, an alkylene group contains one to two carbon atoms ($C_1$-$C_2$ alkylene). In other embodiments, an alkylene group contains one carbon atom ($C_1$ alkylene).

As used herein, the term "alkenyl" refers to a linear or branched-chain monovalent hydrocarbon radical with at least one carbon-carbon double bond. An alkenyl includes radicals having "cis" and "trans" orientations, or alternatively, "E" and "Z" orientations. In one example, the alkenyl radical is a $C_2$-$C_{18}$ group. In other embodiments, the alkenyl radical is a $C_2$-$C_{12}$, $C_2$-$C_{10}$, $C_2$-$C_8$, $C_2$-$C_8$ or $C_2$-$C_3$ group. Examples include ethenyl or vinyl, prop-1-enyl, prop-2-enyl, 2-methylprop-1-enyl, but-1-enyl, but-2-enyl, but-3-enyl, buta-1,3-dienyl, 2-methylbuta-1,3-diene, hex-1-enyl, hex-2-enyl, hex-3-enyl, hex-4-enyl and hexa-1,3-dienyl.

As used herein, the term "alkynyl" refers to a linear or branched monovalent hydrocarbon radical with at least one carbon-carbon triple bond. In one example, the alkynyl radical is a $C_2$-$C_{18}$ group. In other examples, the alkynyl radical is $C_9$-$C_{19}$, $C_2$-$C_{10}$, $C_2$-$C_8$, $C_2$-$C_6$, or $C_2$-$C_3$. Examples include ethynyl prop-1-ynyl, prop-2-ynyl, but-1-ynyl, but-2-ynyl and but-3-ynyl.

The terms "alkoxyl" or "alkoxy" as used herein refer to an alkyl group, as defined above, having an oxygen radical attached thereto, and which is the point of attachment. Representative alkoxyl groups include methoxy, ethoxy, propyloxy, tert-butoxy and the like. An "ether" is two hydrocarbyl groups covalently linked by an oxygen. Accordingly, the substituent of an alkyl that renders that alkyl an ether is or resembles an alkoxyl, such as can be represented by one of —O-alkyl, —O-alkenyl, and —O-alkynyl.

As used herein, the term "halogen" (or "halo" or "halide") refers to fluorine, chlorine, bromine, or iodine.

As used herein, the term "cyclic group" broadly refers to any group that used alone or as part of a larger moiety, contains a saturated, partially saturated or aromatic ring system e.g., carbocyclic (cycloalkyl, cycloalkenyl), heterocyclic (heterocycloalkyl, heterocycloalkenyl), aryl and heteroaryl groups. Cyclic groups may have one or more (e.g., fused) ring systems. Thus, for example, a cyclic group can contain one or more carbocyclic, heterocyclic, aryl or heteroaryl groups.

As used herein, the term "carbocyclic" (also "carbocyclyl") refers to a group that used alone or as part of a larger moiety, contains a saturated, partially unsaturated, or aromatic ring system having 3 to 20 carbon atoms, that is alone or part of a larger moiety (e.g., an alkcarbocyclic group). The term carbocyclyl includes mono-, bi-, tri-, fused, bridged, and spiro-ring systems, and combinations thereof. In one embodiment, carbocyclyl includes 3 to 15 carbon atoms ($C_3$-$C_{15}$). In one embodiment, carbocyclyl includes 3 to 12 carbon atoms ($C_3$-$C_{12}$). In another embodiment, carbocyclyl includes $C_3$-$C_8$, $C_3$-$C_{10}$ or $C_5$-$C_{10}$. In another embodiment, carbocyclyl, as a monocycle, includes $C_3$-$C_8$, $C_3$-$C_6$ or $C_5$-$C_8$. In some embodiments, carbocyclyl, as a bicycle, includes $C_7$-$C_{12}$. In another embodiment, carbocyclyl, as a spiro system, includes $C_5$-$C_{12}$. Representative examples of monocyclic carbocyclyls include cyclopropyl, cyclobutyl, cyclopentyl, 1-cyclopent-1-enyl, 1-cyclopent-2-enyl, 1-cyclopent-3-enyl, cyclohexyl, perdeuteriocyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, phenyl, and cyclododecyl; bicyclic carbocyclyls having 7 to 12 ring atoms include [4,3], [4,4], [4,5], [5,5], [5,6] or [6,6] ring systems, such as for example bicyclo[2.2.1]heptane, bicyclo[2.2.2]octane, naphthalene, and bicyclo[3.2.2]nonane. Representative examples of spiro carbocyclyls include spiro[2.2]pentane, spiro[2.3]hexane, spiro[2.4]heptane, spiro[2.5]octane and spiro[4.5]decane. The term carbocyclyl includes aryl ring systems as defined herein. The term carbocycyl also includes cycloalkyl rings (e.g., saturated or partially unsaturated mono-, bi-, or spiro-carbocycles). The term carbocyclic group also includes a carbocyclic ring fused to one or more (e.g., 1, 2 or 3) different cyclic groups (e.g., aryl or heterocyclic rings), where the radical or point of attachment is on the carbocyclic ring.

Thus, the term carbocyclic also embraces carbocyclylalkyl groups which as used herein refer to a group of the formula —$R^c$-carbocyclyl where $R^c$ is an alkylene chain. The term carbocyclic also embraces carbocyclylalkoxy groups which as used herein refer to a group bonded through an oxygen atom of the formula —O—$R^c$-carbocyclyl where $R^c$ is an alkylene chain.

As used herein, the term "aryl" used alone or as part of a larger moiety (e.g., "aralkyl", wherein the terminal carbon atom on the alkyl group is the point of attachment, e.g., a benzyl group), "aralkoxy" wherein the oxygen atom is the point of attachment, or "aroxyalkyl" wherein the point of attachment is on the aryl group) refers to a group that includes monocyclic, bicyclic or tricyclic, carbon ring system, that includes fused rings, wherein at least one ring in the system is aromatic. In some embodiments, the aralkoxy group is a benzoxy group. The term "aryl" may be used interchangeably with the term "aryl ring". In one embodiment, aryl includes groups having 6-18 carbon atoms. In another embodiment, aryl includes groups having 6-10 carbon atoms. Examples of aryl groups include phenyl, naphthyl, anthracyl, biphenyl, phenanthrenyl, naphthacenyl, 1,2,3,4-tetrahydronaphthalenyl, 1H-indenyl, 2,3-dihydro-1H-indenyl, naphthyridinyl, and the like, which may be substituted or independently substituted by one or more substituents described herein. A particular aryl is phenyl. In some embodiments, an aryl group includes an aryl ring fused to one or more (e.g., 1, 2 or 3) different cyclic groups (e.g., carbocyclic rings or heterocyclic rings), where the radical or point of attachment is on the aryl ring.

Thus, the term aryl embraces aralkyl groups (e.g., benzyl) which as disclosed above refer to a group of the formula —$R^c$-aryl where $R^c$ is an alkylene chain such as methylene or ethylene. In some embodiments, the aralkyl group is an optionally substituted benzyl group. The term aryl also embraces aralkoxy groups which as used herein refer to a group bonded through an oxygen atom of the formula —O—$R^c$-aryl where $R^c$ is an alkylene chain such as methylene or ethylene.

As used herein, the term "heterocyclyl" refers to a "carbocyclyl" that used alone or as part of a larger moiety, contains a saturated, partially unsaturated or aromatic ring system, wherein one or more (e.g., 1, 2, 3, or 4) carbon atoms have been replaced with a heteroatom (e.g., O, N, N(O), S, S(O), or $S(O)_2$). The term heterocyclyl includes mono-, bi-, tri-, fused, bridged, and spino-ring systems, and combinations thereof. In some embodiments, a heterocyclyl refers to a 3 to 15 membered heterocyclyl ring system. In some embodiments, a heterocyclyl refers to a 3 to 12 membered heterocyclyl ring system. In some embodiments, a heterocyclyl refers to a saturated ring system, such as a 3 to 12 membered saturated heterocyclyl ring system. In some embodiments, a heterocyclyl refers to a heteroaryl ring system, such as a 5 to 14 membered heteroaryl ring system. The term heterocyclyl also includes $C_3$-$C_8$ heterocycloalkyl, which is a saturated or partially unsaturated mono-, bi-, or spiro-ring system containing 3-8 carbons and one or more (1, 2, 3 or 4) heteroatoms.

In some embodiments, a heterocyclyl group includes 3-12 ring atoms and includes monocycles, bicycles, tricycles and spiro ring systems, wherein the ring atoms are carbon, and one to 5 ring atoms is a heteroatom such as nitrogen, sulfur or oxygen. In some embodiments, heterocyclyl includes 3- to 7-membered monocycles having one or more heteroatoms selected from nitrogen, sulfur or oxygen. In some embodiments, heterocyclyl includes 4- to 6-membered monocycles having one or more heteroatoms selected from nitrogen, sulfur or oxygen. In some embodiments, heterocyclyl includes 3-membered monocycles. In some embodiments, heterocyclyl includes 4-membered monocycles. In some embodiments, heterocyclyl includes 5-6 membered monocycles. In some embodiments, the heterocyclyl group includes 0 to 3 double bonds. In any of the foregoing embodiments, heterocyclyl includes 1, 2, 3 or 4 heteroatoms. Any nitrogen or sulfur heteroatom may optionally be oxidized (e.g., NO, SO, $SO_2$), and any nitrogen heteroatom may optionally be quaternized (e.g., $[NR_4]^+Cl^-$, $[NR_4]^+OH^-$). Representative examples of heteracyclyls include oxiranyl, aziridinyl, thiiranyl, azetidinyl, oxetanyl, thietanyl, 1,2-dithietanyl, 1,3-dithietanyl, pyrrolidinyl, dihydro-1H-pyrrolyl, dihydrofuranyl, tetrahydropyranyl, dihydrothienyl, tetrahydrothienyl, imidazolidinyl, piperidinyl, piperazinyl, morpholinyl, thiomorpholinyl, 1,1-dioxo-thiomorpholinyl, dihydropyranyl, tetrahydropyranyl, hexahydrothiopyranyl, hexahydropyrimidinyl, oxazinanyl, thiazinanyl, thioxanyl, homopiperazinyl, homopiperidinyl, azepanyl, oxepanyl, thiepanyl, oxazepinyl, oxazepanyl, diazepanyl, 1,4-diazepanyl, diazepinyl, thiazepinyl, thiazepanyl, tetrahydrothiopyranyl, oxazoildinyl, thiazolidinyl, isothiazolidinyl, 1,1-dioxoisothiazolidinonyl, oxazolidinonyl, imidazolidinonyl, 4,5,6,7-tetrahydro[2H]indazolyl, tetrahydrobenzoimidazolyl, 4,5,6,7-tetrahydrobenzo[d]imidazolyl, 1,6-dihydroimidazol[4,5-d]pyrrolo[2,3-b]pyridinyl, thiazinyl, thiophenyl, oxazinyl, thiadiazinyl, oxadiazinyl, dithiazinyl, dioxazinyl, oxathiazinyl, thiatriazinyl, oxatriazinyl, dithiadiazinyl, imidazolinyl, dihydropyrimidyl, tetrahydropyrimidyl, 1-pyrrolinyl, 2-pyrrolinyl, 3-pyrrolinyl, indolinyl, thiapyranyl, 2H-pyranyl, 4H-pyranyl, dioxanyl, 1,3-dioxolanyl, pyrazolinyl, pyrazolidinyl, dithianyl, dithiolanyl, pyrimidinonyl, pyrimidindionyl, pyrimidin-2,4-dionyl, piperazinonyl, piperazindionyl, pyrazolidinylimidazolinyl, 3-azabicyclo[3.1.0]hexanyl, 3,6-diazabicyclo[3.1.1]heptanyl, 6-azabicyclo[3.1.1]heptanyl, 3-azabicyclo[3.1.1]heptanyl, 3-azabicyclo[4.1.0]heptanyl, azabicyclo[2.2.2]hexanyl, 2-azabicyclo[3.2.1]octanyl, 8-azabicyclo[3.2.1]octanyl, 2-azabicyclo[2.2.2]octanyl, 8-azabicyclo[2.2.2]octanyl, 7-oxabicyclo[2.2.1]heptane, azaspiro[3.5]nonanyl, azaspiro[2.5]octanyl, azaspiro[4.5]decanyl, 1-azaspiro[4.5]decan-2-only, azaspiro[5.5]undecanyl, tetrahydroindolyl, octahydmindolyl, tetrahydroisoindolyl, tetrahydroindazolyl, 1,1-dioxohexahydrothiopyranyl. Examples of 5-membered heterocyclyls containing a sulfur or oxygen atom and one to three nitrogen atoms are thiazolyl, including thiazol-2-yl and thiazol-2-yl N-oxide, thiadiazolyl, including 1,3,4-thiadiazol-5-yl and 1,2,4-thiadiazol-5-yl, oxazolyl, for example oxazol-2-yl, and oxadiazolyl, such as 1,3,4-oxadiazol-5-yl, and 1,2,4-oxadiazol-5-yl. Example 5-membered ring heterocyclyls containing 2 to 4 nitrogen atoms include imidazolyl, such as imidazol-2-yl; triazolyl, such as 1,3,4-triazol-5-yl; 1,2,3-triazol-5-yl, 1,2,4-triazol-5-yl, and tetrazolyl, such as 1H-tetrazol-5-yl. Representative examples of benzo-fused 5-membered heterocyclyls are benzoxazol-2-yl, benzthiazol-2-yl and benzimidazol-2-yl. Example 6-membered heterocyclyls contain one to three nitrogen atoms and optionally a sulfur or oxygen atom, for example pyridyl, such as pyrid-2-yl, pyrid-3-yl, and pyrid-4-yl; pyrimidyl, such as pyrimid-2-yl and pyrimid-4-yl; triazinyl, such as 1,3,4-triazin-2-yl and 1,3,5-triazin-4-yl; pyridazinyl, in particular pyridazin-3-yl, and pyrazinyl. The pyridine N-oxides and pyridazine N-oxides and the pyridyl, pyrimid-2-yl, pyrimid-4-yl, pyridazinyl and the 1,3,4-triazin-2-yl groups, are yet other examples of heterocyclyl groups. In some embodiments, a heterocyclic group includes a heterocyclic ring fused to one or more (e.g., 1, 2 or 3) different cyclic groups (e.g., carbocyclic rings or heterocyclic rings), where the radical or point of attachment is on the heterocyclic ring, and in some embodiments wherein the point of attachment is a heteroatom contained in the heterocyclic ring.

Thus, the term heterocyclic embraces N-heterocyclyl groups which as used herein refer to a heterocyclyl group containing at least one nitrogen and where the point of attachment of the heterocyclyl group to the rest of the molecule is through a nitrogen atom in the heterocyclyl group. Representative examples of N-heterocyclyl groups include 1-morpholinyl, 1-piperidinyl, 1-piperazinyl, 1-pyrrolidinyl, pyrazolidinyl, imidazolinyl and imidazolidinyl. The term heterocyclic also embraces C-heterocyclyl groups which as used herein refer to a heterocyclyl group containing at least one heteroatom and where the point of attachment of the heterocyclyl group to the rest of the molecule is through a carbon atom in the heterocyclyl group. Representative examples of C-heterocyclyl radicals include 2-morpholinyl, 2- or 3- or 4-piperidinyl, 2-piperazinyl, and 2- or 3-pyrrolidinyl. The term heterocyclic also embraces heterocyclylalkyl groups which as disclosed above refer to a group of the formula —$R^c$-heterocyclyl where $R^c$ is an alkylene chain. The term heterocyclic also embraces heterocyclylalkoxy groups which as used herein refer to a radical bonded through an oxygen atom of the formula —O—$R^c$-heterocyclyl where $R^c$ is an alkylene chain.

As used herein, the term "heteroaryl" used alone or as part of a larger moiety (e.g., "heteroarylalkyl" (also "heteroaralkyl"), or "heteroarylalkoxy" (also "heteroaralkoxy"), refers to a monocyclic, bicyclic or tricyclic ring system having 5 to 14 ring atoms, wherein at least one ring is aromatic and contains at least one heteroatom. In one embodiment, heteroaryl includes 5-5 membered monocyclic aromatic groups where one or more ring atoms is nitrogen, sulfur or oxygen. Representative examples of heteroaryl groups include thienyl, furyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, imidazopyridyl, pyrazinyl, pyridazinyl, triazinyl, tetrazinyl, tetrazolo[1,5-b]pyridazinyl, purinyl, deazapurinyl, benzoxazolyl, benzofuryl, benzothiazolyl, benzothiadiazolyl, benzotriazolyl, benzoimidazolyl, indolyl, 1,3-thiazol-2-yl, 1,3,4-triazol-5-yl, 1,3-oxazol-2-yl, 1,3,4-oxadiazol-5-yl, 1,2,4-oxadiazol-5-yl, 1,3,4-thiadiazol-5-yl, 1H-tetrazol-5-yl, 1,2,3-triazol-5-yl, and pyrid-2-yl N-oxide. The term "heteroaryl" also includes groups in which a heteroaryl is fused to one or more cyclic (e.g., carbocyclyl, or heterocyclyl) rings, where the radical or point of attachment is on the heteroaryl ring. Nonlimiting examples include indolyl, indolizinyl, isoindolyl, benzothienyl, benzothiophenyl, methylenedioxyphenyl, benzofuranyl, dibenzofuranyl, indazolyl, benzimidazolyl, benzodioxazolyl, benzthiazolyl, quinolyl, isoquinolyl, cinnolinyl, phthalazinyl, quiriazolinyl, quinoxalinyl, carbazolyl, acridinyl, phenazinyl, phenothiazinyl, phenoxazinyl, tetrahydroquinolinyl, tetrahydroisoquinolinyl and pyrido[2,3-b]-1,4-oxazin-3(4H)-one. A heteroaryl group may be mono-, bi- or tri-cyclic. In some embodiments, a heteroaryl group includes a heteroaryl ring fused to one or more (e.g., 1, 2 or 3) different cyclic groups (e.g., carbocyclic rings or heterocyclic rings), where the radical or point of attachment is on the heteroaryl ring, and in some embodiments wherein the point of attachment is a heteroatom contained in the heterocyclic ring.

Thus, the term heteroaryl embraces N-heteroaryl groups which as used herein refer to a heteroaryl group as defined above containing at least one nitrogen and where the point of attachment of the heteroaryl group to the rest of the molecule is through a nitrogen atom in the heteroaryl group. The term heteroaryl also embraces C-heteroaryl groups which as used herein refer to a heteroaryl group as defined above and where the point of attachment of the heteroaryl group to the rest of the molecule is through a carbon atom in the heteroaryl group. The term heteroaryl also embraces heteroarylalkyl groups which as disclosed above refer to a group of the formula —$R^c$-heteroaryl, wherein $R^c$ is an alkylene chain as defined above. The term heteroaryl also embraces heteroaralkoxy (or heteroarylalkoxy) groups which as used herein refer to a group bonded through an oxygen atom of the formula —O—$R^c$-heteroaryl, where $R^c$ is an alkylene group as defined above.

Unless stated otherwise, and to the extent not further defined for any particular group(s), any of the groups described herein may be substituted or unsubstituted. As used herein, the term "substituted" broadly refers to all permissible substituents with the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc. Representative substituents include halogens, hydroxyl groups, and any other organic groupings containing any number of carbon atoms, e.g., 1-14 carbon atoms, and which may include one or more (e.g., 1, 2, 3, or 4) heteroatoms such as oxygen, sulfur, and nitrogen grouped in a linear, branched, or cyclic structural format.

To the extent not disclosed otherwise for any particular group(s), representative examples of substituents may include alkyl, substituted alkyl (e.g., $C_1$-$C_6$, $C_1$-$C_5$, $C_1$-$C_4$, $C_1$-$C_3$, $C_1$-$C_2$, $C_1$), alkoxy (e.g., $C_1$-$C_5$, $C_1$-$C_4$, $C_1$-$C_3$, $C_1$-$C_2$, $C_1$, substituted alkoxy (e.g., $C_1$-$C_6$, $C_1$-$C_6$, $C_1$-$C_3$, $C_1$-$C_2$, $C_1$), haloalkyl (e.g., $CF_3$), alkenyl (e.g., $C_2$-$C_6$, $C_2$-$C_5$, $C_2$-$C_4$, $C_2$-$C_3$, $C_2$), substituted alkenyl (e.g., $C_2$-$C_6$, $C_2$-$C_5$, $C_2$-$C_4$, $C_2$-$C_3$, $C_2$), alkynyl (e.g., $C_2$-$C_6$, $C_2$-$C_5$, $C_2$-$C_4$, $C_2$-$C_3$, $C_2$), substituted alkynyl (e.g., $C_2$-$C_6$, $C_2$-$C_5$, $C_2$-$C_4$, $C_2$-$C_3$, $C_2$), cyclic (e.g., $C_3$-$C_{12}$, $C_5$-$C_6$), substituted cyclic (e.g., $C_3$-$C_{12}$, $C_5$-$C_6$, carbocyclic (e.g., $C_3$-$C_{12}$, $C_5$-$C_6$), substituted carbocyclic (e.g., $C_3$-$C_{12}$, $C_3$-$C_6$), heterocyclic (e.g., $C_3$-$C_{12}$, $C_5$-$C_6$), substituted heterocyclic (e.g., $C_3$-$C_{12}$, $C_5$-$C_6$), aryl (e.g., benzyl and phenyl), substituted aryl (e.g., substituted benzyl or phenyl), heteroaryl (e.g., pyridyl or pyrimidyl), substituted heteroaryl (e.g., substituted pyridyl or pyrimidyl), aralkyl (e.g., benzyl), substituted aralkyl (e.g., substituted benzyl), halo, hydroxyl, aryloxy (e.g., $C_6$-$C_{12}$, $C_6$), substituted aryloxy (e.g., $C_6$-$C_{12}$, $C_6$), alkylthio (e.g., $C_1$-$C_6$), substituted alkylthio (e.g., $C_1$-$C_6$), arylthio (e.g., $C_6$-$C_1$, $C_6$), substituted arylthio (e.g., $C_6$-$C_{12}$, $C_6$), cyano, carbonyl, substituted carbonyl, carboxyl, substituted carboxyl, amino, substituted amino, amido, substituted amido, thio, substituted thio, sulfinyl, substituted sulfinyl, sulfonyl, substituted sulfonyl, sulfinamide, substituted sulfinamide, sulfonamide, substituted sulfonamide, urea, substituted urea, carbamate, substituted carbamate, amino acid, and peptide groups.

In one aspect, provided herein are compounds represented by formula (I):

(I)

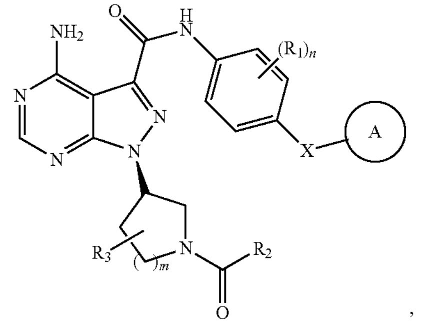

or a pharmaceutically acceptable salt or stereoisomer thereof, wherein:

X is absent, —$CH_2$—, —O—, or C(O);

A is absent, naphthyl, 5-membered heterocyclyl containing 1-3 heteroatoms selected from N, O, and S, or fused-heterobicyclyl having 5- or 6-membered rings and containing 1-4 heteroatoms selected from N, O, and S, and wherein A is optionally substituted with one or more $R_4$;

each $R_A$ is independently $C_1$-$C_6$ alkyl, $C_1$-$C_6$ haloalkyl, $C_1$-$C_6$ alkoxy, $C_1$-$C_6$ haloalkoxy, halo, hydroxyl, cyano, nitro, amino, $C_1$-$C_6$ alkylamino, or di-$C_1$-$C_6$ alkylamino;

each $R_1$ is independently $C_1$-$C_6$ alkyl, $C_2$-$C_6$ alkenyl, $C_1$-$C_6$ haloalkyl, $C_1$-$C_6$ alkoxy, $C_1$-$C_6$ haloalkoxy, $C_1$-$C_6$ alkylamido, halo, hydroxyl, cyano, nitro, amino, $C_1$-$C_6$ alkylamino, $C_1$-$C_1$-$C_6$ alkylamino, $C_3$-$C_6$ carbocyclyl, or 5- or 6-membered heterocyclyl, wherein $R_1$ is optionally substituted with one or more $R_A$, or two $R_1$ groups together with the atoms to which they are attached form a 5- to 6-membered carbocyclyl or heterocyclyl;

$R_2$ is

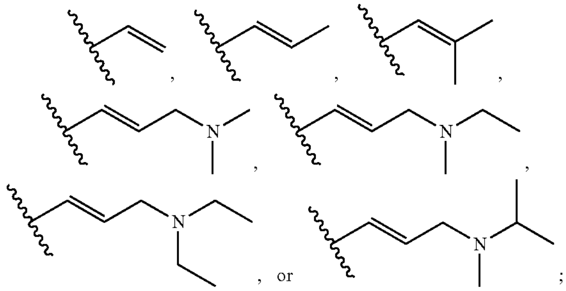

$R_3$ is hydrogen, fluoro, or methyl;

m is 1 or 2; and n is 0, 1, or 2.

In some embodiments, X is absent.

In some embodiments, X is —$CH_2$—.

In some embodiments, X is —O—.

In some embodiments, X is C(O).

In some embodiments, A is naphthyl optionally substituted with one or more $R_A$.

In some embodiments, A is fused heterobicyclyl having a 5- and a 6-membered ring and contains 1-4 heteroatoms selected from N, O, and S, wherein A is optionally substituted with one or more $R_A$.

In some embodiments, A is fused heterobicyclyl comprising two 6-membered rings and contains 1-4 heteroatoms selected from N, O, and S, wherein A is optionally substituted with one or more $R_A$.

In some embodiments, A is 5-membered heterocyclyl containing 1-3 heteroatoms selected from N, O, and S, and that is optionally substituted with one or more $R_A$.

In some embodiments, A is

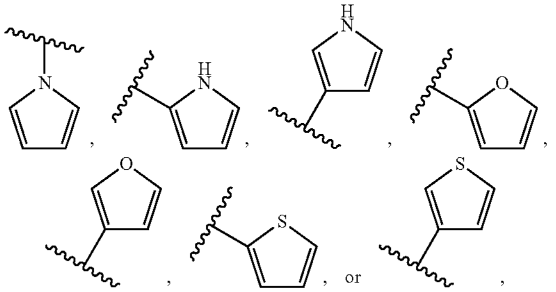

and is optionally substituted with one or more $R_A$.

In some embodiments, A is

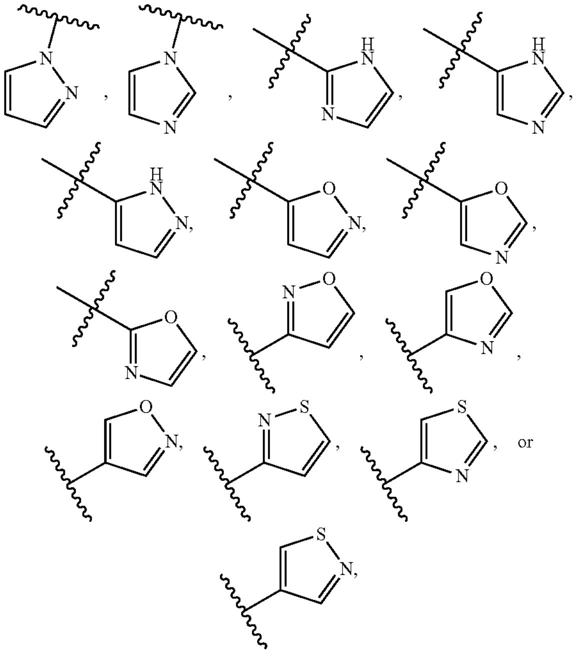

and is optionally substituted with one or more $R_A$.

In some embodiments, A is

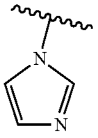 [SMILES: *n1ccnc1]

optionally substituted with one or more $R_A$.

In some embodiments, A is

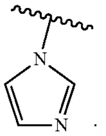

In some embodiments, A is

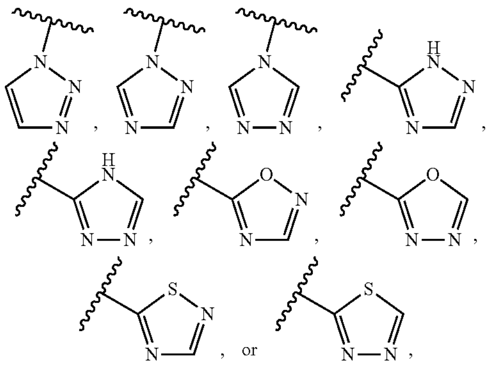

and is optionally substituted with one or more $R_A$.

In some embodiments, A is
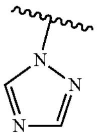 [SMILES: *n1cncn1]
optionally substituted with one or more $R_A$.
In some embodiments, A is
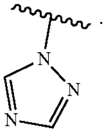
.
In some embodiments, A is
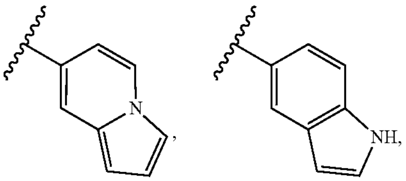
, ,
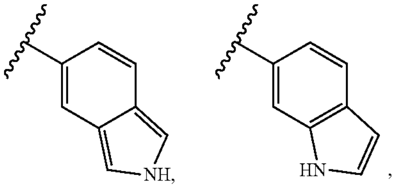
, , or
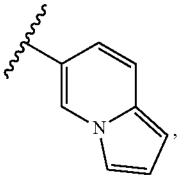
,
and is optionally substituted with one or more $R_A$.
In some embodiments, A is
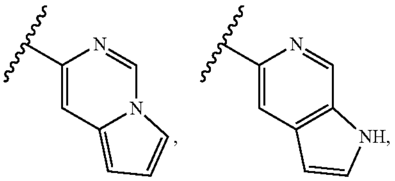
, ,
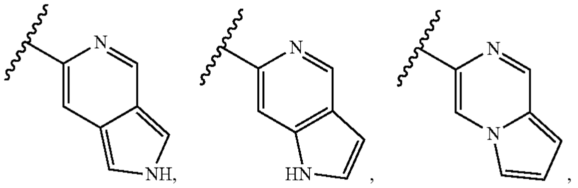
, , ,
-continued
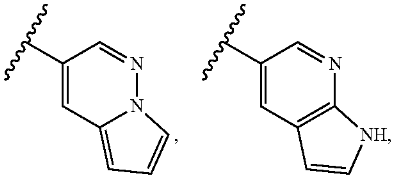
, ,
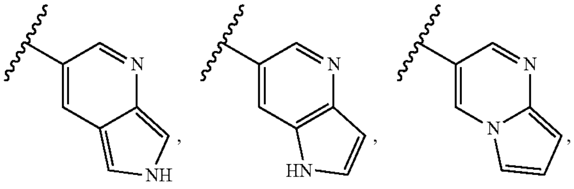
, , ,
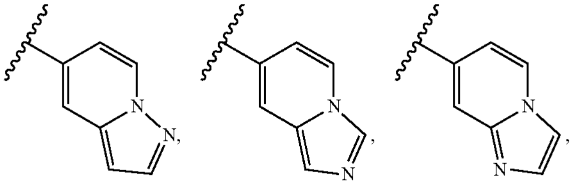
, , ,
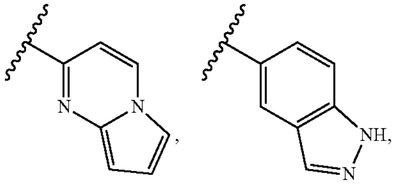
, ,
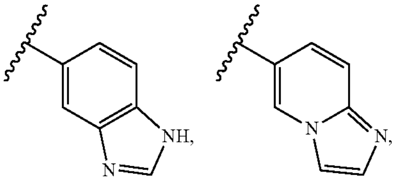
, ,
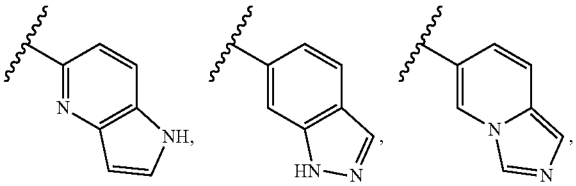
, , ,
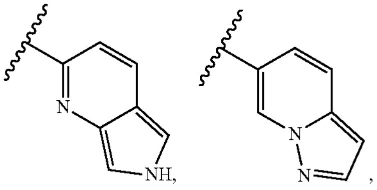
, , or
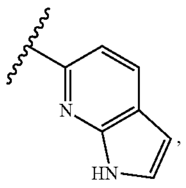
,
and is optionally substituted with one or more $R_A$.

In some embodiments, A is
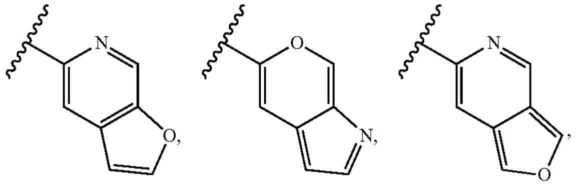
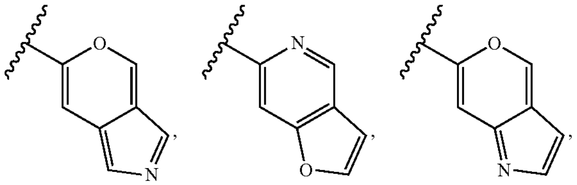
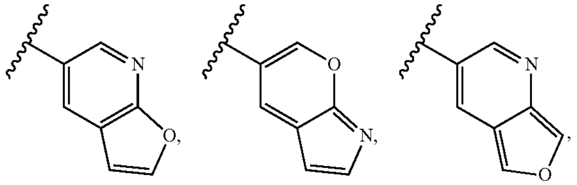
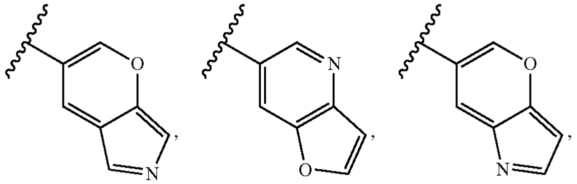
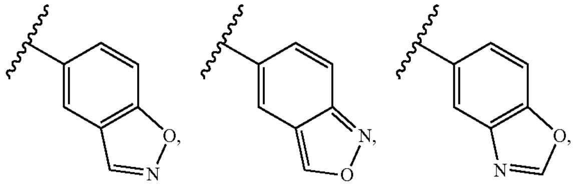
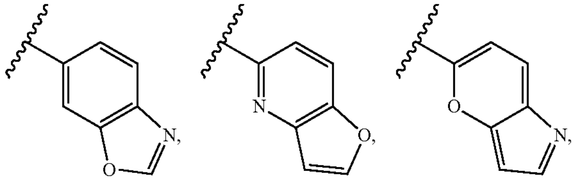
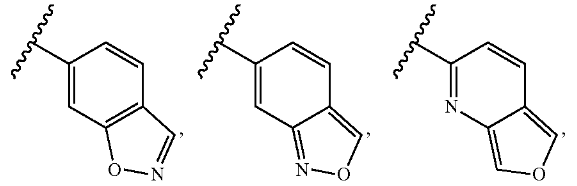
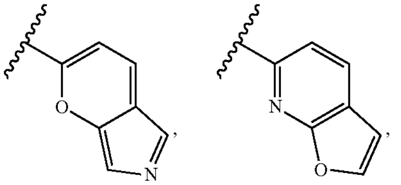
or
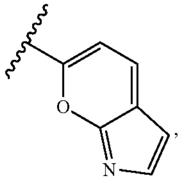
and is optionally substituted with one or more $R_A$.
In some embodiments, A is
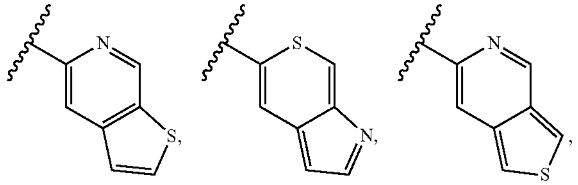
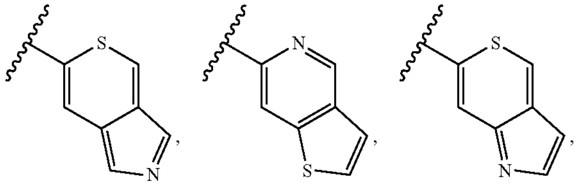
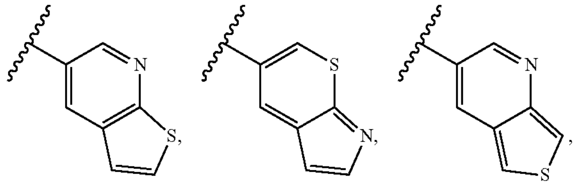
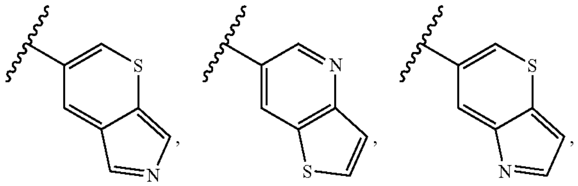
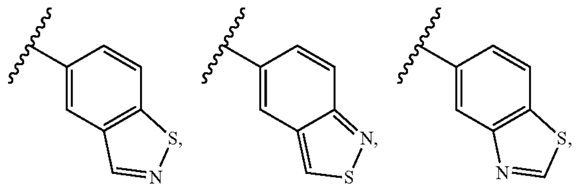
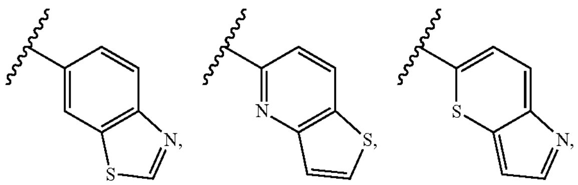
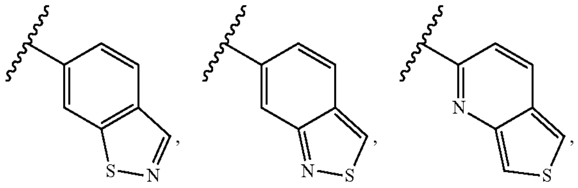
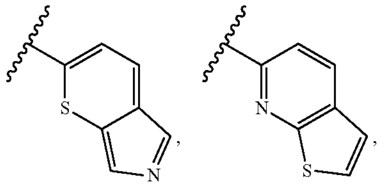
or -continued
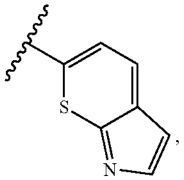
and is optionally substituted with one or more $R_A$.
In some embodiments, A is
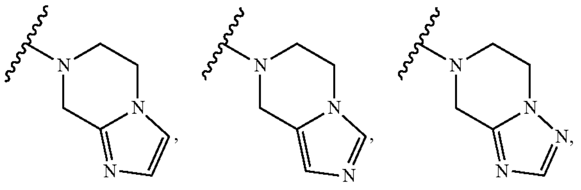
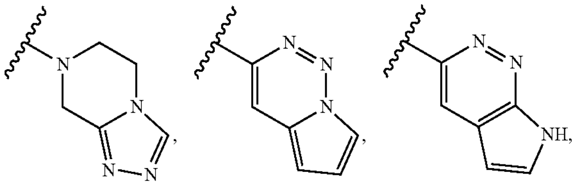
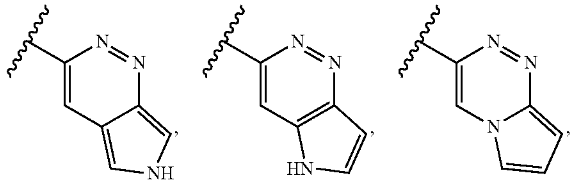
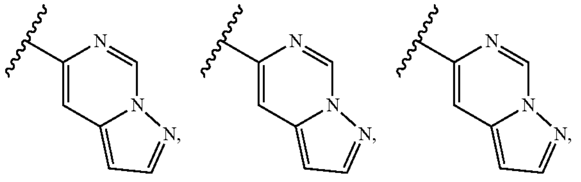
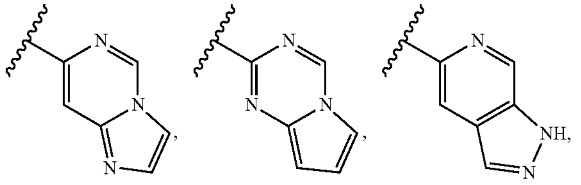
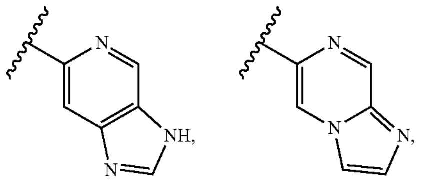
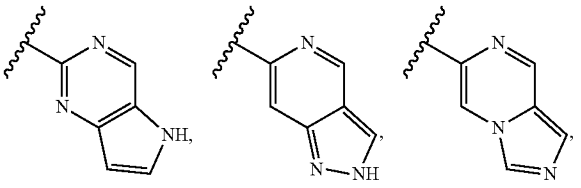
-continued
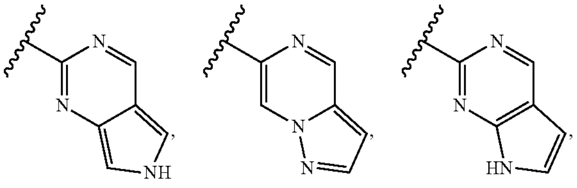
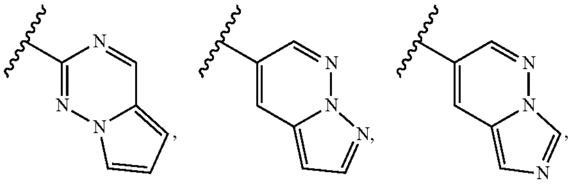
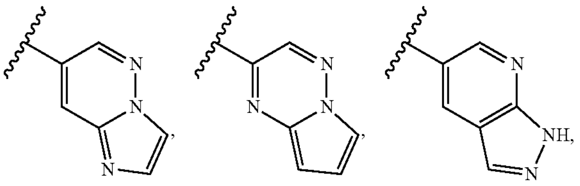
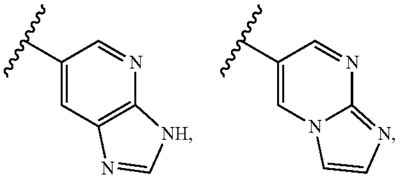
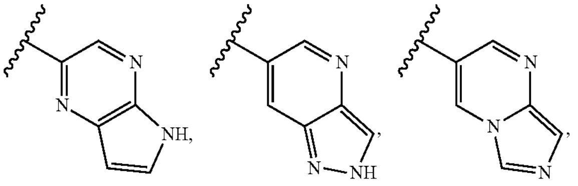
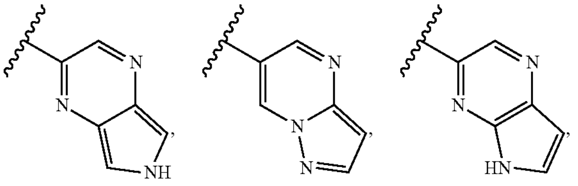
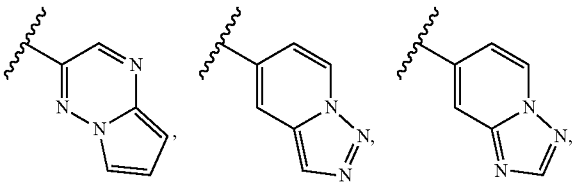
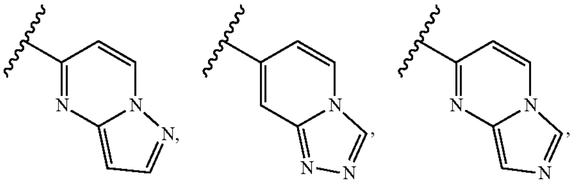
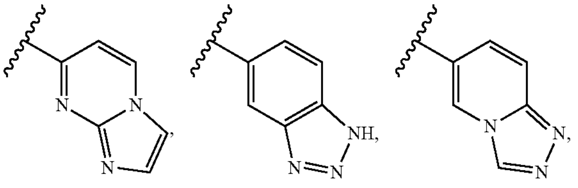

-continued

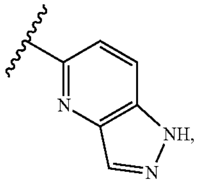, 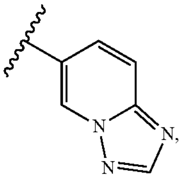,

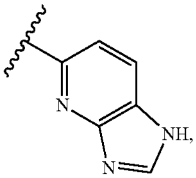, 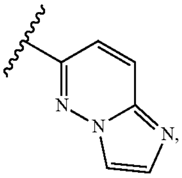, 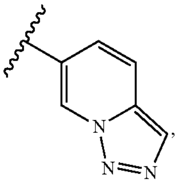,

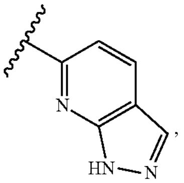, 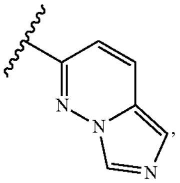, or

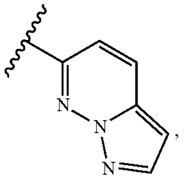, and is optionally substituted with one or more $R_A$.

In some embodiments, A is

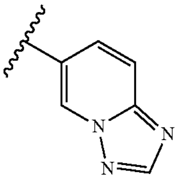 [SMILES: *c1ccc2ncnn2c1]

optionally substituted with one or more $R_A$.

In some embodiments, A is

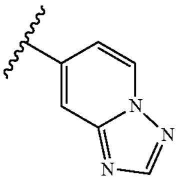 [SMILES: *c1ccn2ncnc2c1]

optionally substituted with one or more $R_A$.

In some embodiments, A is

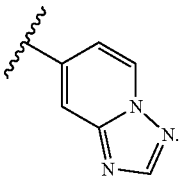 [SMILES: *c1ccn2ncnc2c1].

In some embodiments, A is

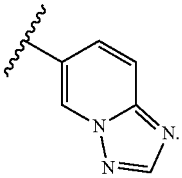 [SMILES: *c1ccc2ncnn2c1].

In some embodiments, A is

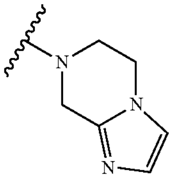 [SMILES: *N1CCn2ccnc2C1]

optionally substituted with one or more $R_A$.

In some embodiments, A is

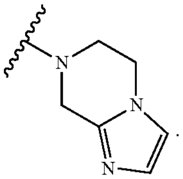 [SMILES: *N1CCn2ccnc2C1].

In some embodiments, A is

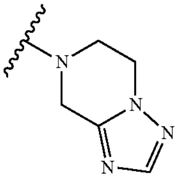 or 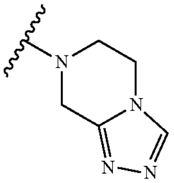, and is optionally substituted with one or more $R_A$.

In some embodiments, A is

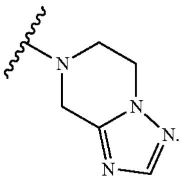.

In some embodiments, A is

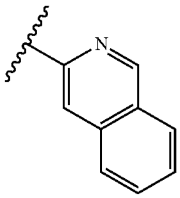,
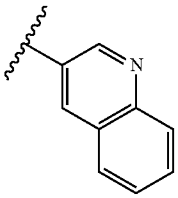,
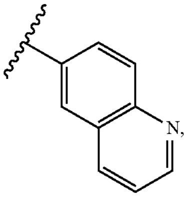,
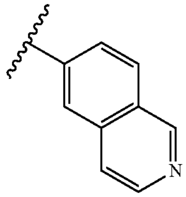,
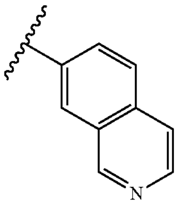,
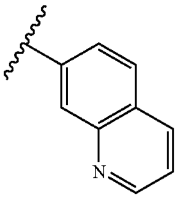, or
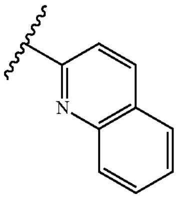, and is optionally substituted with one or more $R_A$.

In some embodiments, $R_1$ is independently $C_1$-$C_6$ alkyl, $C_2$-$C_6$ alkenyl, $C_1$-$C_6$ alkoxy, $C_1$-$C_6$ haloalkoxy, $C_1$-$C_6$ alkylamido, halo, cyano, di-$C_1$-$C_6$ alkylamino, $C_3$-$C_6$carbocyclyl, or 5- or 6-membered heterocyclyl.

In some embodiments, $R_1$ is independently methyl, ethyl, fluoro, chloro, bromo, methoxy, cyano, —$OCHF_2$, —$OCH_2F$, —$NMe_2$,

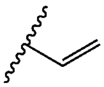,
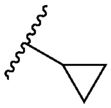,
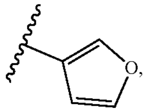,
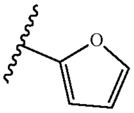, or
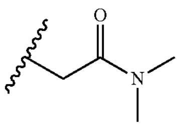.

In some embodiments, $R_1$ is methyl.

In some embodiments, $R_1$ is chloro.

In some embodiments, $R_1$ is

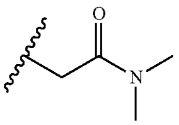.

In some embodiments, two $R_1$ groups together with the atoms to which they are attached form a 5- to 6-membered carbocyclyl or heterocyclyl.

In some embodiments, two $R_1$ groups together with the atoms to which they are attached form phenyl, pyridinyl, or dioxolane.

In some embodiments, $R_2$ is

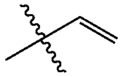.

In some embodiments, $R_3$ is hydrogen.

In some embodiments, m is 2.

In some embodiments, n is 1.

In some embodiments, n is 2.

In some embodiments, the compound of formula I is of formula Ia-Ih:

(Ia)

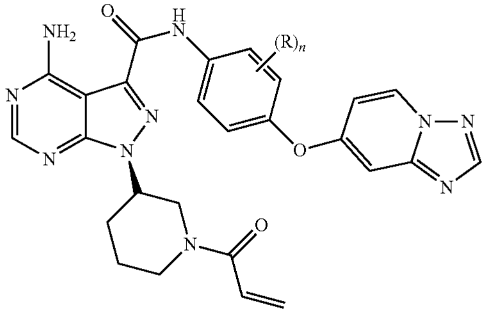, (Ib)

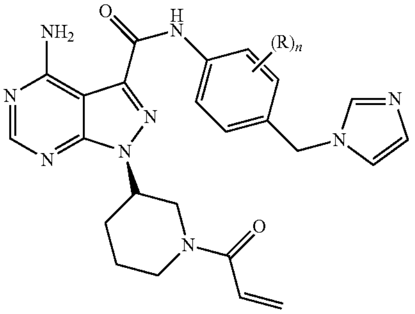, (Ic)

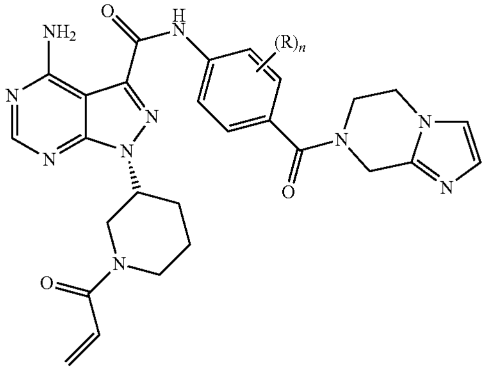,

-continued
(Id)
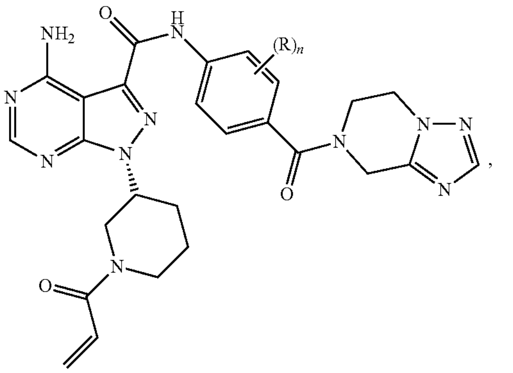
(Ie)
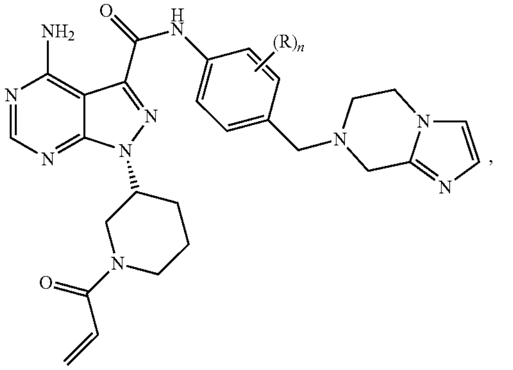
(If)
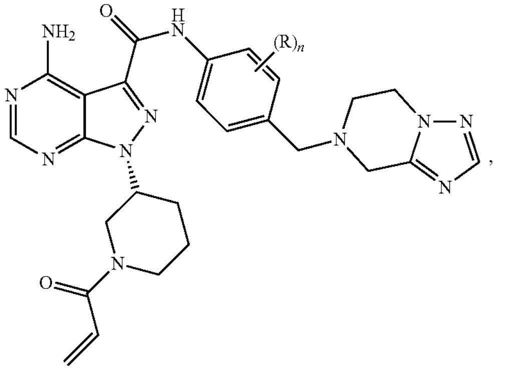
(Ig)
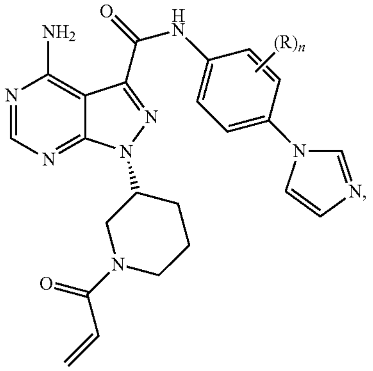
-continued
(Ih)
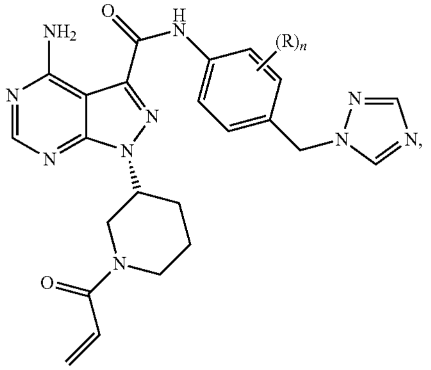
or a pharmaceutically acceptable salt or stereoisomer thereof.
In some embodiments of formula Ia-Ih, $R_1$ is methyl.
In some embodiments of formula Ia-Ih, $R_1$ is chloro.
In some embodiments of formula Ia-Ih, n is 1.
In some embodiments of formula Ia-Ih, n is 2.
Representative compounds of formula (I) have the following structures:
(1)
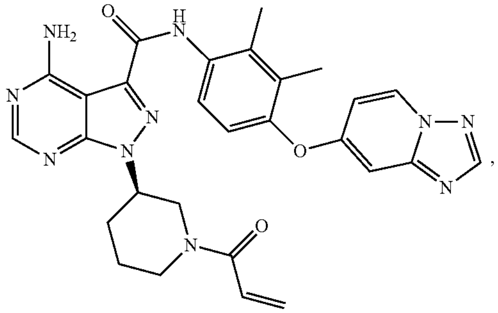
(2)
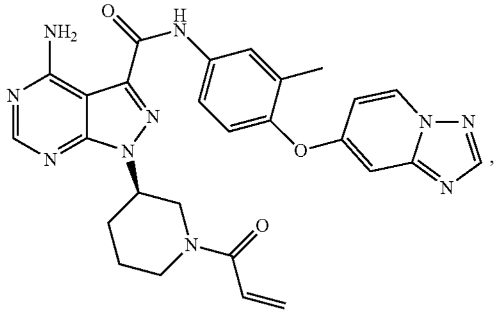
(3)
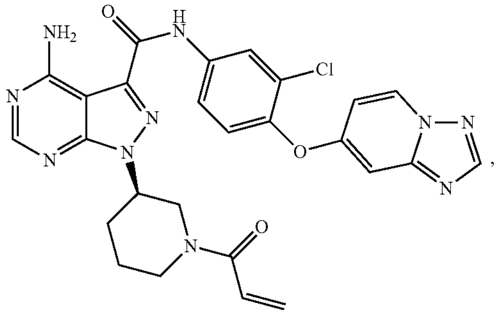

-continued (4)

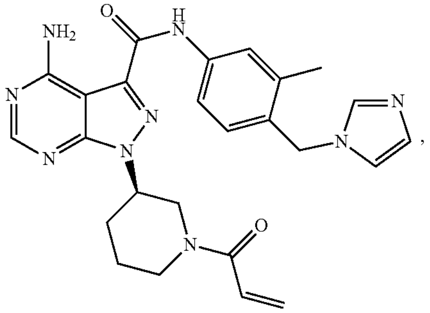

(5)

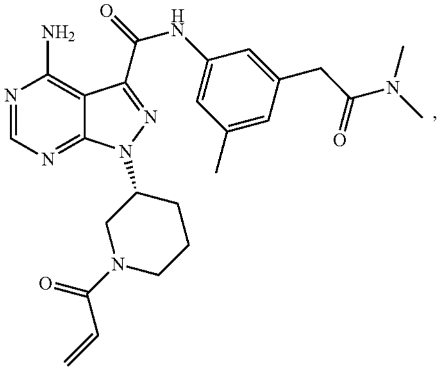

(6)

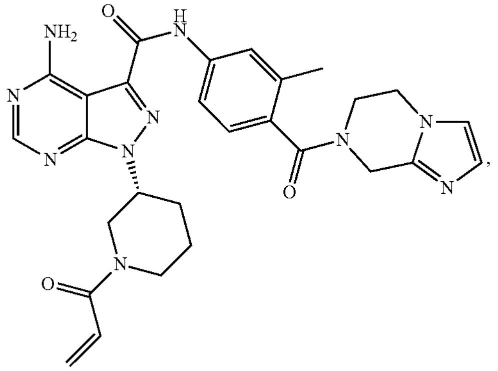

(7)

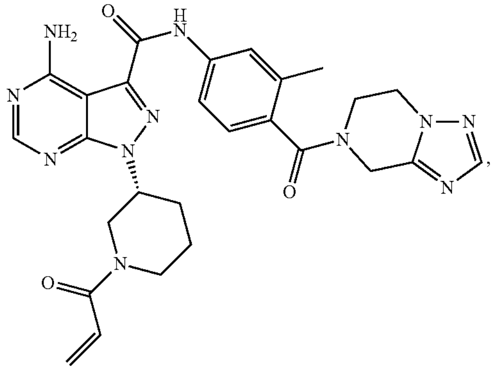

-continued (8)

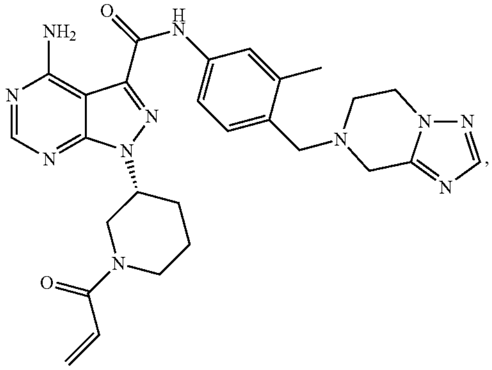

(9)

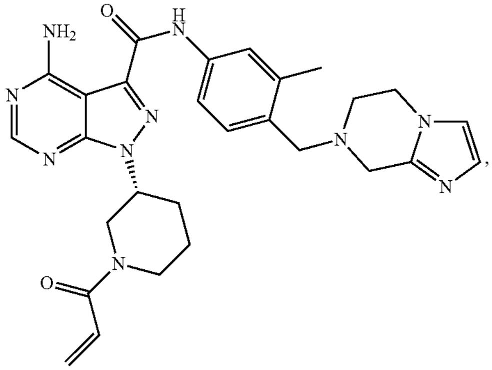

(10)

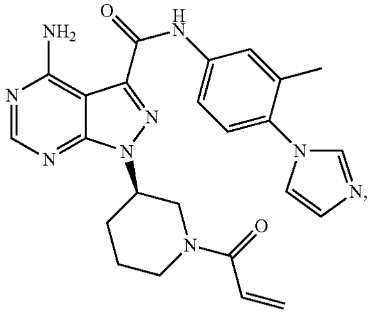

or (11)

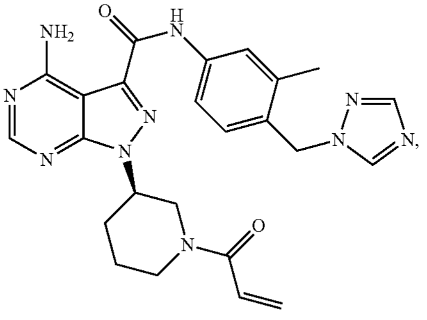

or a pharmaceutically acceptable salt or stereoisomer thereof.

Compounds of the present disclosure may be in the form of a free acid or free base, or a pharmaceutically acceptable salt. As used herein, the term "pharmaceutically acceptable" in the context of a salt refers to a salt of the compound that does not abrogate the biological activity or properties of the compound, and is relatively nontoxic, i.e., the compound in salt form may be administered to a subject without causing undesirable biological effects (such as dizziness or gastric upset) or interacting in a deleterious manner with any of the other components of the composition in which it is contained. The term “pharmaceutically acceptable salt” refers to a product obtained by reaction of the compound of the present disclosure with a suitable acid or a base. Examples of pharmaceutically acceptable salts of the compounds of this disclosure include those derived from suitable inorganic bases such as Li, Na, K, Ca, Mg, Fe, Cu, Al, Zn and Mn salts. Examples of pharmaceutically acceptable, nontoxic acid addition salts are salts of an amino group formed with inorganic acids such as hydrochloride, hydrobromide, hydroiodide, nitrate, sulfate, bisulfate, phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesuffonate, benzenesulfonate, 4-methylbenzenesulfonate or p-toluenesulfonate salts and the like. Certain compounds provided herein can form pharmaceutically acceptable salts with various organic bases such as lysine, arginine, guanidine, diethanolamine or metformin. Suitable base salts include aluminum, calcium, lithium, magnesium, potassium, sodium, or zinc salts.

Compounds of the present disclosure may have at least one chiral center and thus may be in the form of a stereoisomer, which, as used herein, embraces all isomers of individual compounds that differ only in the orientation of their atoms in space. The term stereoisomer includes mirror image isomers (enantiomers which include the (R-) or (S-) configurations of the compounds), mixtures of mirror image isomers (physical mixtures of the enantiomers, and racemates or racemic mixtures) of compounds, geometric (cis/trans or E/Z, R/S) isomers of compounds and isomers of compounds with more than one chiral center that are not mirror images of one another (diastereoisomers). The chiral centers of the compounds may undergo epimerization in vivo; thus, for these compounds, administration of the compound in its (R-) form is considered equivalent to administration of the compound in its (S-) form. Accordingly, the compounds of the present disclosure may be made and used in the form of individual isomers and substantially free of other isomers, or in the form of a mixture of various isomers, e.g., racemic mixtures of stereoisomers.

In some embodiments, the compound is an isotopic derivative in that it has at least one desired isotopic substitution of an atom, at an amount above the natural abundance of the isotope, i.e., enriched. In one embodiment, the compound includes deuterium or multiple deuterium atoms. Substitution with heavier isotopes such as deuterium, i.e. $^2H$, may afford certain therapeutic advantages resulting from greater metabolic stability, for example, increased in vivo half-life or reduced dosage requirements, and thus may be advantageous in some circumstances.

The compounds of the present disclosure may be prepared by crystallization under different conditions and may exist as one or a combination of polymorphs of the compound. For example, different polymorphs may be identified and/or prepared using different solvents, or different mixtures of solvents for recrystallization, by performing crystallizations at different temperatures, or by using various modes of cooling, ranging from very fast to very slow cooling during crystallizations. Polymorphs may also be obtained by heating or melting the compound followed by gradual or fast cooling. The presence of polymorphs may be determined by solid probe NMR spectroscopy, IR spectroscopy, differential scanning calorimetry, powder X-ray diffractogram and/or other known techniques.

In some embodiments, the pharmaceutical composition comprises a co-crystal of an inventive compound. The term “co-crystal”, as used herein, refers to a stoichiometric multicomponent system comprising a compound provided herein and a co-crystal former wherein the compound provided herein and the co-crystal former are connected by non-covalent interactions. The term “co-crystal former”, as used herein, refers to compounds which can form intermolecular interactions with a compound provided herein and co-crystallize with it. Representative examples of co-crystal formers include benzoic acid, succinic acid, fumaric acid, glutaric acid, trans-cinnamic acid, 2,5-dihydroxybenzoic acid, glycolic acid, trans-2-hexanoic acid, 2-hydroxycaproic acid, lactic acid, sorbic acid, tartaric acid, ferulic acid, suberic acid, picolinic acid, salicyclic acid, maleic acid, saccharin, 4,4'-bipyridine p-aminosalicyclic acid, nicotinamide, urea, isonicotinamide, methyl-4-hydroxybenzoate, adipic acid, terephthalic acid, resorcinol, pyrogallol, phloroglucinol, hydroxyquinol, isoniazid, theophylline, adenine, theobromine, phenacetin, phenazone, etofylline, and phenobarbital.

Methods of Synthesis

In another aspect, the present disclosure is directed to a method for making an inventive compound, or a pharmaceutically acceptable salt or stereoisomer thereof. Broadly, the inventive compounds or a pharmaceutically acceptable salt or stereoisomer thereof may be prepared by any process known to be applicable to the preparation of chemically related compounds. The compounds of the present disclosure will be better understood in connection with the synthetic schemes that described in various working examples and which illustrate non-limiting methods by which the compounds of the disclosure may be prepared.

Pharmaceutical Compositions

Another aspect of the present disclosure is directed to a pharmaceutical composition that includes a therapeutically effective amount of an inventive compound or a pharmaceutically acceptable salt or stereoisomer thereof, and a pharmaceutically acceptable carrier. The term “pharmaceutically acceptable carrier,” as known in the art, refers to a pharmaceutically acceptable material, composition or vehicle, suitable for administering compounds of the present disclosure to mammals. Suitable carriers may include, for example, liquids (both aqueous and non-aqueous alike, and combinations thereof), solids, encapsulating materials, gases, and combinations thereof (e.g., semi-solids), and gases, that function to carry or transport the compound from one organ, or portion of the body, to another organ, or portion of the body. A carrier is “acceptable” in the sense of being physiologically inert to and compatible with the other ingredients of the formulation and not injurious to the subject or patient. Depending on the type of formulation, the composition may also include one or more pharmaceutically acceptable excipients.

Broadly, compounds of the present disclosure and their pharmaceutically acceptable salts, or stereoisomers may be formulated into a given type of composition in accordance with conventional pharmaceutical practice such as conventional mixing, dissolving, granulating, dragee-making, levigating, emulsifying, encapsulating, entrapping and compression processes (see, e.g., Remington: *The Science and Practice of Pharmacy* (20th ed.), ed. A. R. Gennaro, Lippincott Williams & Wilkins, 2000 and *Encyclopedia of Pharmaceutical Technology*, eds. J. Swarbrick and J. C. Boylan, 1988-1999, Marcel Dekker, New York). The type of formulation depends on the mode of administration which may include enteral (e.g., oral, buccal, sublingual and rectal), parenteral (e.g., subcutaneous (s.c.), intravenous (i.v.), intramuscular (i.m.), and intrasternal injection, or infusion techniques, intra-ocular, intra-arterial, intramedullary, intrathecal, intraventricular, transdermal, interdermal, intravaginal, intraperitoneal, mucosal, nasal, intratracheal instillation, bronchial instillation, and inhalation) and topical (e.g., transdermal). In general, the most appropriate route of administration will depend upon a variety of factors including, for example, the nature of the agent (e.g., its stability in the environment of the gastrointestinal tract), and/or the condition of the subject (e.g., whether the subject is able to tolerate oral administration). For example, parenteral (e.g., intravenous) administration may also be advantageous in that the compound may be administered relatively quickly such as in the case of a single-dose treatment and/or an acute condition.

In some embodiments, the compounds are formulated for oral or intravenous administration (e.g., systemic intravenous injection).

Accordingly, compounds provided herein may be formulated into solid compositions (e.g., powders, tablets, dispersible granules, capsules, cachets, and suppositories), liquid compositions (e.g., solutions in which the compound is dissolved, suspensions in which solid particles of the compound are dispersed, emulsions, and solutions containing liposomes, micelles, or nanoparticles, syrups and elixirs); semi-solid compositions (e.g., gels, suspensions and creams); and gases (e.g., propellants for aerosol compositions). Compounds may also be formulated for rapid, intermediate or extended release.

Solid dosage forms for oral administration include capsules, tablets, pills, powders, and granules. In such solid dosage forms, the active compound is mixed with a carrier such as sodium citrate or dicalcium phosphate and an additional carrier or excipient such as a) fillers or extenders such as starches, lactose, sucrose, glucose, mannitol, and silicic acid, b) binders such as, for example, methylcellulose, microcrystalline cellulose, hydroxypropylmethylcellulose, carboxymethylcellulose, sodium carboxymethylcellulose, alginates, gelatin, polyvinylpyrrolidinone, sucrose, and acacia, c) humectants such as glycerol, d) disintegrating agents such as crosslinked polymers (e.g., crosslinked polyvinylpyrrolidone (crospovidone), crosslinked sodium carboxymethyl cellulose (croscarmellose sodium), sodium starch glycolate, agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also include buffering agents. Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings. They may further contain an opacifying agent.

In some embodiments, compounds provided herein may be formulated in a hard or soft gelatin capsule. Representative excipients that may be used include pregelatinized starch, magnesium stearate, mannitol, sodium stearyl fumarate, lactose anhydrous, microcrystalline cellulose and croscarmellose sodium. Gelatin shells may include gelatin, titanium dioxide, iron oxides and colorants.

Liquid dosage forms for oral administration include solutions, suspensions, emulsions, micro-emulsions, syrups and elixirs. In addition to the compound, the liquid dosage forms may contain an aqueous or non-aqueous carrier (depending upon the solubility of the compounds) commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Oral compositions may also include any excipients such as wetting agents, suspending agents, coloring, sweetening, flavoring, and perfuming agents.

Injectable preparations for parenteral administration may include sterile aqueous solutions or oleaginous suspensions. They may be formulated according to standard techniques using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. The effect of the compound may be prolonged by slowing its absorption, which may be accomplished by the use of a liquid suspension or crystalline or amorphous material with poor water solubility. Prolonged absorption of the compound from a parenterally administered formulation may also be accomplished by suspending the compound in an oily vehicle.

In certain embodiments, compounds provided herein may be administered in a local rather than systemic manner, for example, via injection of the conjugate directly into an organ, often in a depot preparation or sustained release formulation. In specific embodiments, long acting formulations are administered by implantation (for example subcutaneously or intramuscularly) or by intramuscular injection. Injectable depot forms are made by forming microencapsule matrices of the compound in a biodegradable polymer, e.g., polylactide-polyglycolides, poly(orthoesters) and poly(anhydrides). The rate of release of the compound may be controlled by varying the ratio of compound to polymer and the nature of the particular polymer employed. Depot injectable formulations are also prepared by entrapping the compound in liposomes or microemulsions that are compatible with body tissues. Furthermore, in other embodiments, the compound is delivered in a targeted drug delivery system, for example, in a liposome coated with organ-specific antibody. In such embodiments, the liposomes are targeted to and taken up selectively by the organ.

The compositions may be formulated for buccal or sublingual administration, examples of which include tablets, lozenges and gels.

The compounds provided herein may be formulated for administration by inhalation. Various forms suitable for administration by inhalation include aerosols, mists or powders. Pharmaceutical compositions may be delivered in the form of an aerosol spray presentation from pressurized packs or a nebulizer, with the use of a suitable propellant (e.g., dichlorodifluoromethane, trichlorofluoromethane, dichlorotetrafluoroethane, carbon dioxide or other suitable gas). In some embodiments, the dosage unit of a pressurized aerosol may be determined by providing a valve to deliver a metered amount. In some embodiments, capsules and cartridges including gelatin, for example, for use in an inhaler or insufflator, may be formulated containing a powder mix of the compound and a suitable powder base such as lactose or starch.

Compounds provided herein may be formulated for topical administration which as used herein, refers to administration intradermally by the formulation to the epidermis. These types of compositions are typically in the form of ointments, pastes, creams, lotions, gels, solutions and sprays.

Representative examples of carriers useful in formulating compounds for topical application include solvents (e.g., alcohols, poly alcohols, water), creams, lotions, ointments, oils, plasters, liposomes, powders, emulsions, microemulsions, and buffered solutions (e.g., hypotonic or buffered saline). Creams, for example, may be formulated using saturated or unsaturated fatty acids such as stearic acid, palmitic acid, oleic acid, palmito-oleic acid, cetyl, or oleyl alcohols. Creams may also contain a non-ionic surfactant such as polyoxy-40-stearate.

In some embodiments, the topical formulations may also include an excipient, an example of which is a penetration enhancing agent. These agents are capable of transporting a pharmacologically active compound through the stratum corneum and into the epidermis or dermis, preferably, with little or no systemic absorption. A wide variety of compounds have been evaluated as to their effectiveness in enhancing the rate of penetration of drugs through the skin. See, for example, *Percutaneous Penetration Enhancers*, Maibach H. I. and Smith H. E. (eds.), CRC Press, Inc., Boca Raton, Fla. (1995), which surveys the use and testing of various skin penetration enhancers, and Buyuktimkin et al., *Chemical Means of Transdermal Drug Permeation Enhancement in Transdermal and Topical Drug Delivery Systems*, Gosh T. K., Pfister W. R., Yum S. I. (Eds.), Interpharm Press Inc., Buffalo Grove, III. (1997). Representative examples of penetration enhancing agents include triglycerides (e.g., soybean oil), aloe compositions (e.g., aloe-vera gel), ethyl alcohol, isopropyl alcohol, octolyphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate), and N-methylpyrrolidone.

Representative examples of yet other excipients that may be included in topical as well as in other types of formulations (to the extent they are compatible), include preservatives, antioxidants, moisturizers, emollients, buffering agents, solubilizing agents, skin protectants, and surfactants. Suitable preservatives include alcohols, quaternary amines, organic acids, parabens, and phenols. Suitable antioxidants include ascorbic acid and its esters, sodium bisulfite, butylated hydroxytoluene, butylated hydroxyanisole, tocopherols, and chelating agents like EDTA and citric acid. Suitable moisturizers include glycerin, sorbitol, polyethylene glycols, urea, and propylene glycol. Suitable buffering agents include citric, hydrochloric, and lactic acid buffers. Suitable solubilizing agents include quaternary ammonium chlorides, cyclodextrins, benzyl benzoate, lecithin, and polysorbates. Suitable skin protectants include vitamin E oil, allatoin, dimethicone, glycerin, petrolatum, and zinc oxide.

Transdermal formulations typically employ transdermal delivery devices and transdermal delivery patches wherein the compound is formulated in lipophilic emulsions or buffered, aqueous solutions, dissolved and/or dispersed in a polymer or an adhesive. Patches may be constructed for continuous, pulsatile, or on demand delivery of pharmaceutical agents. Transdermal delivery of the compounds may be accomplished by means of an iontophoretic patch. Transdermal patches may provide controlled delivery of the compounds wherein the rate of absorption is slowed by using rate-controlling membranes or by trapping the compound within a polymer matrix or gel. Absorption enhancers may be used to increase absorption, examples of which include absorbable pharmaceutically acceptable solvents that assist passage through the skin.

Ophthalmic formulations include eye drops.

Formulations for rectal administration include enemas, rectal gels, rectal foams, rectal aerosols, and retention enemas, which may contain conventional suppository bases such as cocoa butter or other glycerides, as well as synthetic polymers such as polyvinylpyrrolidone, PEG, and the like. Compositions for rectal or vaginal administration may also be formulated as suppositories which can be prepared by mixing the compound with suitable non-irritating carriers and excipients such as cocoa butter, mixtures of fatty acid glycerides, polyethylene glycol, suppository waxes, and combinations thereof, all of which are solid at ambient temperature but liquid at body temperature and therefore melt in the rectum or vaginal cavity and release the compound.

Dosage Amounts

As used herein, the term. "therapeutically effective amount" refers to an amount of an inventive compound or a pharmaceutically acceptable salt or stereoisomer thereof that is effective in producing the desired therapeutic response in a patient suffering from a disease or disorder that is characterized or mediated by aberrant human epidermal growth factor receptor 2 (Her2) activity. The term "therapeutically effective amount" thus includes the amount of the inventive compound or a pharmaceutically acceptable salt or stereoisomer thereof, that when administered, induces a positive modification in the disease or disorder to be treated, or is sufficient to prevent development or progression of the disease or disorder, or alleviate to some extent, one or more of the symptoms of the disease or disorder being treated in a subject, or inhibits the growth of diseased cells, or reduces the amounts of HER2 in diseased cells.

The total daily dosage of the compounds and usage thereof may be decided in accordance with standard medical practice, e.g., by the attending physician using sound medical judgment. The specific therapeutically effective dose for any particular subject will depend upon a variety of factors, including the following: the disease or disorder being treated and the severity thereof (e.g., its present status); the activity of the compound employed; the specific composition employed; the age, body weight, general health, sex and diet of the subject; the time of administration, route of administration, and rate of excretion of the compound employed; the duration of the treatment: drugs used in combination or coincidental with the specific compound employed; and like factors well known in the medical arts (see, for example, Hardman et at, eds., *Goodman and Gilman's The Pharmacological Basis of Therapeutics,* 10th Edition, McGraw-Hill Press, 155-173, 2001).

Compounds provided herein may be effective over a wide dosage range. In some embodiments, the total daily dosage (e.g., for adult humans) may range from about 0.001 to about 1600 mg, from 0.01 to about 1000 mg, from 0.01 to about 500 mg, from about 0.01 to about 100 mg, from about 0.5 to about 100 mg, from 1 to about 100-400 mg per day, from about 1 to about 50 mg per day, from about 5 to about 40 mg per day, and in yet other embodiments from about 10 to about 30 mg per day. Individual dosages may be formulated to contain the desired dosage amount depending upon the number of times the compound is administered per day. By way of example, capsules may be formulated with from about 1 to about 200 mg of compound (e.g., 1, 2, 2.5, 3, 4, 5, 10, 15, 20, 25, 50, 100, 150, and 200 mg). In some embodiments, the compound may be administered at a dose in range from about 0.01 mg to about 200 mg/kg of body weight per day. In some embodiments, a dose of from 0.1 to 100, e.g., from 1 to 30 mg/kg per day in one or more dosages per day may be effective. By way of example, a suitable dose for oral administration may be in the range of 1-30 mg/kg of body weight per day, and a suitable dose for intravenous administration may be in the range of 1-10 mg/kg of body weight per day.

Methods of Use

In some aspects, the present disclosure is directed to methods of treating diseases or disorders involving HER2, that entails administration of a therapeutically effective amount of a compound of formula (I), or a pharmaceutically acceptable salt or stereoisomer thereof, to a subject in need thereof.

Broadly, the diseases or disorders that may be amenable to treatment with compounds of the present disclosure involve HER2 or otherwise functionally abnormal HER2 activity relative to a non-pathological state. A "disease" is generally regarded as a state of health of a subject wherein the subject cannot maintain homeostasis, and wherein if the disease is not ameliorated then the subject's health continues to deteriorate. In contrast, a "disorder" in a subject is a state of health in which the subject is able to maintain homeostasis, but in which the subject's state of health is less favorable than it would be in the absence of the disorder. Left untreated, a disorder does not necessarily cause a further decrease in the subject's state of health. In some embodiments, compounds of formula (I) may be useful in the treatment of cell proliferative diseases and disorders (e.g., cancer or benign neoplasms). As used herein, the term "cell proliferative disease or disorder" refers to the conditions characterized by deregulated or abnormal cell growth, or both, including noncancerous conditions such as neoplasms, precancerous conditions, benign tumors, and cancer.

In some embodiments, the disease or disorder is characterized or mediated by activity of a HER2 mutant.

In some embodiments, the HER2 mutant is an exon 20 insertion mutant.

The term "subject" (or 'patient') as used herein includes all members of the animal kingdom prone to or suffering from the indicated disease or disorder. In some embodiments, the subject is a mammal, e.g., a human or a non-human mammal. The methods are also applicable to companion animals such as dogs and cats as well as livestock such as cows, horses, sheep, goats, pigs, and other domesticated and wild animals. A subject "in need of" treatment according to the present disclosure may be "suffering from or suspected of suffering from" a specific disease or disorder may have been positively diagnosed or otherwise presents with a sufficient number of risk factors or a sufficient number or combination of signs or symptoms such that a medical professional could diagnose or suspect that the subject was suffering from the disease or disorder. Thus, subjects suffering from, and suspected of suffering from, a specific disease or disorder are not necessarily two distinct groups.

Exemplary types of non-cancerous (e.g., cell proliferative) diseases or disorders that may be amenable to treatment with the compounds of the present disclosure include inflammatory diseases and conditions, autoimmune diseases, neurodegenerative diseases, heart diseases, viral diseases, chronic and acute kidney diseases or injuries, metabolic diseases, and allergic and genetic diseases.

Representative examples of specific non-cancerous diseases and disorders include rheumatoid arthritis, alopecia areata, lymphoproliferative conditions, autoimmune hematological disorders (e.g. hemolytic anemia, aplastic anemia, anhidrotic ectodermal dysplasia, pure red cell anemia and idiopathic thrombocytopenia), cholecystitis, acromegaly, rheumatoid spondylitis, osteoarthritis, gout, scleroderma, sepsis, septic shock, dacryoadenitis, cryopyrin associated periodic syndrome (CAPS), endotoxic shock, endometritis, gram-negative sepsis, keratoconjunctivitis sicca, toxic shock syndrome, asthma, adult respiratory distress syndrome, chronic obstructive pulmonary disease, chronic pulmonary inflammation, chronic graft rejection, hidradenitis suppurativa, inflammatory bowel disease, Crohn's disease, Behcet's syndrome, systemic lupus erythematosus, glomerulonephritis, multiple sclerosis, juvenile-onset diabetes, autoimmune uveoretinitis, autoimmune vasculitis, thyroiditis, Addison's disease, lichen planus, appendicitis, bullous pemphigus, pemphigus vulgaris, pemphigus foliaceus, paraneoplastic pemphigus, myasthenia gravis, immunoglobulin A nephropathy, Hashimoto's disease, Sjogren's syndrome, vitiligo, Wegener granulomatosis, granulomatous orchitis, autoimmune oophoritis, sarcoidosis, rheumatic carditis, ankylosing spondylitis, Grave's disease, autoimmune thrombocytopenic purpura, psoriasis, psoriatic arthritis, eczema, dermatitis herpetiformis, ulcerative colitis, pancreatic fibrosis, hepatitis, hepatic fibrosis, CD14 mediated sepsis, non-CD14 mediated sepsis, acute and chronic renal disease, irritable bowel syndrome, pyresis, restenosis, cervicitis, stroke and ischemic injury, neural trauma, acute and chronic pain, allergic rhinitis, allergic conjunctivitis, chronic heart failure, congestive heart failure, acute coronary syndrome, cachexia, malaria, leprosy, leishmaniosis, Lyme disease, Reiter's syndrome, acute synovitis, muscle degeneration, bursitis, tendonitis, tenosynovitis, herniated, ruptured, or prolapsed intervertebral disk syndrome, osteopetrosis, rhinosinusitis, thrombosis, silicosis, pulmonary sarcosis, bone resorption diseases, such as osteoporosis, fibromyalgia, AIDS and other viral diseases such as Herpes Zoster, Herpes Simplex I or II, influenza virus and cytomegalovirus, diabetes Type I and II, obesity, insulin resistance and diabetic retinopathy, 22q11.2 deletion syndrome, Angelman syndrome, Canavan disease, celiac disease, Charcot-Marie-Tooth disease, color blindness, Cri du chat, Down syndrome, cystic fibrosis, Duchenne muscular dystrophy, haemophilia, Klinefleter's syndrome, neurofibromatosis, phenylketonuria, Prader-Willi syndrome, sickle cell disease, Tay-Sachs disease, Turner syndrome, urea cycle disorders, thalassemia, otitis, pancreatitis, parotitis, pericarditis, peritonitis, pharyngitis, pleuritis, phlebitis, pneumonitis, uveitis, polymyositis, proctitis, interstitial lung fibrosis, dermatomyositis, atherosclerosis, arteriosclerosis, amyotrophic lateral sclerosis, asociality, varicosis, vaginitis, depression, and Sudden Infant Death Syndrome.

In other embodiments, the methods are directed to treating subjects having cancer. Generally, the compounds of the present disclosure may be effective in the treatment of carcinomas (solid tumors including both primary and metastatic tumors), sarcomas, melanomas, and hematological cancers (cancers affecting blood including lymphocytes, bone marrow and/or lymph nodes) such as leukemia, lymphoma and multiple myeloma. Adult tumors/cancers and pediatric tumors/cancers are included. The cancers may be vascularized, or not yet substantially vascularized, or non-vascularized tumors.

Representative examples of cancers includes adrenocortical carcinoma, AIDS-related cancers (e.g., Kaposi's and AIDS-related lymphoma), appendix cancer, childhood cancers (e.g., childhood cerebellar astrocytoma, childhood cerebral astrocytoma), basal cell carcinoma, skin cancer (non-melanoma), biliary cancer, extrahepatic bile duct cancer, intrahepatic bile duct cancer, bladder cancer, urinary bladder cancer, brain cancer (e.g., gliomas and glioblastomas such as brain stem glioma, gestational trophoblastic tumor glioma, cerebellar astrocytoma, cerebral astrocytoma/malignant glioma, ependymoma, medulloblastoma, supratentorial primitive neuroectodeimal tumors, visual pathway and hypothalamic glioma), breast cancer, bronchial adenomas/carcinoids, carcinoid tumor, nervous system cancer (e.g., central nervous system cancer, central nervous system lymphoma), cervical cancer, chronic myeloproliferative disorders, colorectal cancer (e.g., colon cancer, rectal cancer), polycythemia vera, lymphoid neoplasm, mycosis fungoids, Sezary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastrointestinal cancer (e.g., stomach cancer, small intestine cancer, gastrointestinal carcinoid tumor, gastrointestinal stromal tumor (GIST)), germ cell tumor, ovarian germ cell tumor, head and neck cancer, Hodgkin's lymphoma, leukemia, lymphoma, multiple myeloma, hepatocellular carcinoma, hypopharyngeal cancer, intraocular melanoma, ocular cancer, islet cell tumors (endocrine pancreas), renal cancer (e.g., Wilm's Tumor, clear cell renal cell carcinoma), liver cancer, lung cancer (e.g., non-small cell lung cancer and small cell lung cancer), Waldenstrom's macroglobulinemia, melanoma, intraocular (eye) melanoma, merkel cell carcinoma, mesothelioma, metastatic squamous neck cancer with occult primary, multiple endocrine neoplasia (MEN), myelodysplastic syndromes, essential thrombocythemia, myelodysplastic/myeloproliferative diseases, nasopharyngeal cancer, neuroblastoma, oral cancer (e.g., mouth cancer, lip cancer, oral cavity cancer, tongue cancer, oropharyngeal cancer, throat cancer, laryngeal cancer), ovarian cancer (e.g., ovarian epithelial cancer, ovarian germ cell tumor, ovarian low malignant potential tumor), pancreatic cancer, islet cell pancreatic cancer, paranasal sinus and nasal cavity cancer, parathyroid cancer, penile cancer, pharyngeal cancer, pheochromocytoma, pineoblastoma, pituitary tumor, plasma cell neoplasm, pleuropulmonary blastoma, prostate cancer, retinoblastoma rhabdomyosarcoma, salivary gland cancer, uterine cancer (e.g., endometrial uterine cancer, uterine sarcoma, uterine corpus cancer), squamous cell carcinoma, testicular cancer, thymoma, thymic carcinoma, thyroid cancer, transitional cell cancer of the renal pelvis and ureter and other urinary organs, urethral cancer, gestational trophoblastic tumor, vaginal cancer and vulvar cancer.

Sarcomas that may be treatable with compounds of the present disclosure include both soft tissue and bone cancers alike, representative examples of which include osteosarcoma or osteogenic sarcoma (bone) (e.g., Ewing's sarcoma), chondrosarcoma (cartilage), leiomyosarcoma (smooth muscle), rhabdomyosarcoma (skeletal muscle), mesothelial sarcoma or mesothelioma (membranous lining of body cavities), fibrosarcoma (fibrous tissue), angiosarcoma or hemangioendothelioma (blood vessels), liposarcoma (adipose tissue), glioma or astrocytoma (neurogenic connective tissue found in the brain), myxosarcoma (primitive embryonic connective tissue) and mesenchymous or mixed mesodermal tumor (mixed connective tissue types).

In some embodiments, methods of the present disclosure entail treatment of subjects having cell proliferative diseases or disorders of the hematological system, liver, brain, lung, colon, pancreas, prostate, ovary, breast, skin, and endometrium.

As used herein, "cell proliferative diseases or disorders of the hematological system" include lymphoma, leukemia, myeloid neoplasms, mast cell neoplasms, myelodysplasia, benign monoclonal gammopathy, polycythemia vera, chronic myelocytic leukemia, agnogenic myeloid metaplasia, and essential thrombocythemia. Representative examples of hematologic cancers may thus include multiple myeloma, lymphoma (including T-cell lymphoma, Hodgkin's lymphoma, non-Hodgkin's lymphoma (diffuse large B-cell lymphoma (DLBCL), follicular lymphoma (FL), mantle cell lymphoma (MCL) and ALK+ anaplastic large cell lymphoma (e.g., B-cell non-Hodgkin's lymphoma selected from diffuse large B-cell lymphoma (e.g., germinal center B-cell-like diffuse large B-cell lymphoma or activated B-cell-like diffuse large B-cell lymphoma), Burkitt's lymphoma/leukemia, mantle cell lymphoma, mediastinal (thymic) large B-cell lymphoma, follicular lymphoma, marginal zone lymphoma, lymphoplasmacytic lymphoma/Waldenstrom macroglobulinemia, metastatic pancreatic adenocarcinoma, refractory B-cell non-Hodgkin's lymphoma, and relapsed B-cell non-Hodgkin's lymphoma, childhood lymphomas, and lymphomas of lymphocytic and cutaneous origin, e.g., small lymphocytic lymphoma, leukemia, including childhood leukemia, hairy-cell leukemia, acute lymphocytic leukemia, acute myelocytic leukemia, acute myeloid leukemia (e.g., acute monocytic leukemia), chronic lymphocytic leukemia, small lymphocytic leukemia, chronic myelocytic leukemia, chronic myelogenous leukemia, and mast cell leukemia, myeloid neoplasms and mast cell neoplasms.

As used herein, "cell proliferative diseases or disorders of the liver" include all forms of cell proliferative disorders affecting the liver. Cell proliferative disorders of the liver may include liver cancer (e.g., hepatocellular carcinoma, intrahepatic cholangiocarcinoma and hepatoblastoma), a precancer or precancerous condition of the liver, benign growths or lesions of the liver, and malignant growths or lesions of the liver, and metastatic lesions in tissue and organs in the body other than the liver. Cell proliferative disorders of the liver may include hyperplasia, metaplasia, and dysplasia of the liver.

As used herein, "cell proliferative diseases or disorders of the brain" include all forms of cell proliferative disorders affecting the brain. Cell proliferative disorders of the brain may include brain cancer (e.g., gliomas, glioblastomas, meningiomas, pituitary adenomas, vestibular schwannomas, and primitive neuroectodermal tumors (medulloblastomas)), a precancer or precancerous condition of the brain, benign growths or lesions of the brain, and malignant growths or lesions of the brain, and metastatic lesions in tissue and organs in the body other than the brain. Cell proliferative disorders of the brain may include hyperplasia, metaplasia, and dysplasia of the brain.

As used herein, "cell proliferative diseases or disorders of the lung" include all forms of cell proliferative disorders affecting lung cells. Cell proliferative disorders of the lung include lung cancer, precancer and precancerous conditions of the lung, benign growths or lesions of the lung, hyperplasia, metaplasia, and dysplasia of the lung, and metastatic lesions in the tissue and organs in the body other than the lung. Lung cancer includes all forms of cancer of the lung, e.g., malignant lung neoplasms, carcinoma in situ, typical carcinoid tumors, and atypical carcinoid tumors. Lung cancer includes small cell lung cancer ("SLCL"), non-small cell lung cancer ("NSCLC"), squamous cell carcinoma, adenocarcinoma, small cell carcinoma, large cell carcinoma, squamous cell carcinoma, and mesothelioma. Lung cancer can include "scar carcinoma," bronchoalveolar carcinoma, giant cell carcinoma, spindle cell carcinoma, and large cell neuroendocrine carcinoma. Lung cancer also includes lung neoplasms having histologic and ultrastructural heterogeneity (e.g., mixed cell types). In some embodiments, compounds of the present disclosure may be used to treat non-metastatic or metastatic lung cancer (e.g., NSCLC, ALK-positive NSCLC, NSCLC harboring ROS1 Rearrangement, Lung Adenocarcinoma, and Squamous Cell Lung Carcinoma).

As used herein, "cell proliferative diseases or disorders of the colon" include all forms of cell proliferative disorders affecting colon cells, including colon cancer, a precancer or precancerous conditions of the colon, adenomatous polyps of the colon and metachronous lesions of the colon. Colon cancer includes sporadic and hereditary colon cancer, malignant colon neoplasms, carcinoma in situ, typical carcinoid tumors, and atypical carcinoid tumors, adenocarcinoma, squamous cell carcinoma, and squamous cell carcinoma. Colon cancer can be associated with a hereditary syndrome such as hereditary nonpolyposis colorectal cancer, familiar adenomatous polyposis, MYH associated polyposis, Gardner's syndrome, Peutz-Jeghers syndrome, Turcot's syndrome and juvenile polyposis. Cell proliferative disorders of the colon may also be characterized by hyperplasia, metaplasia, or dysplasia of the colon.

As used herein, "cell proliferative diseases or disorders of the pancreas" include all forms of cell proliferative disorders affecting pancreatic cells. Cell proliferative disorders of the pancreas may include pancreatic cancer, a precancer or precancerous condition of the pancreas, hyperplasia of the pancreas, dysplasia of the pancreas, benign growths or lesions of the pancreas, and malignant growths or lesions of the pancreas, and metastatic lesions in tissue and organs in the body other than the pancreas. Pancreatic cancer includes all forms of cancer of the pancreas, including ductal adenocarcinoma, adenosquamous carcinoma, pleomorphic giant cell carcinoma, mucinous adenocarcinoma, osteoclast-like giant cell carcinoma, mucinous cystadenocarcinoma, acinar carcinoma, unclassified large cell carcinoma, small cell carcinoma, pancreatoblastoma, papillary neoplasm, mucinous cystadenoma, papillary cystic neoplasm, and serous cystadenoma, and pancreatic neoplasms having histologic and ultrastructural heterogeneity (e.g., mixed cell types).

As used herein, "cell proliferative diseases or disorders of the prostate" include all forms of cell proliferative disorders affecting the prostate. Cell proliferative disorders of the prostate may include prostate cancer, a precancer or precancerous condition of the prostate, benign growths or lesions of the prostate, and malignant growths or lesions of the prostate, and metastatic lesions in tissue and organs in the body other than the prostate. Cell proliferative disorders of the prostate may include hyperplasia, metaplasia, and dysplasia of the prostate.

As used herein, "cell proliferative diseases or disorders of the ovary" include all forms of cell proliferative disorders affecting cells of the ovary. Cell proliferative disorders of the ovary may include a precancer or precancerous condition of the ovary, benign growths or lesions of the ovary, ovarian cancer, and metastatic lesions in tissue and organs in the body other than the ovary. Cell proliferative disorders of the ovary may include hyperplasia, metaplasia, and dysplasia of the ovary.

As used herein, "cell proliferative diseases or disorders of the breast" include all forms of cell proliferative disorders affecting breast cells. Cell proliferative disorders of the breast may include breast cancer, a precancer or precancerous condition of the breast, benign growths or lesions of the breast, and metastatic lesions in tissue and organs in the body other than the breast. Cell proliferative disorders of the breast may include hyperplasia, metaplasia, and dysplasia of the breast.

As used herein, "cell proliferative diseases or disorders of the skin" include all forms of cell proliferative disorders affecting skin cells. Cell proliferative disorders of the skin may include a precancer or precancerous condition of the skin, benign growths or lesions of the skin, melanoma, malignant melanoma or other malignant growths or lesions of the skin, and metastatic lesions in tissue and organs in the body other than the skin. Cell proliferative disorders of the skin may include hyperplasia, metaplasia, and dysplasia of the skin.

As used herein, "cell proliferative diseases or disorders of the endometrium" include all forms of cell proliferative disorders affecting cells of the endometrium. Cell proliferative disorders of the endometrium may include a precancer or precancerous condition of the endometrium, benign growths or lesions of the endometrium, endometrial cancer, and metastatic lesions in tissue and organs in the body other than the endometrium. Cell proliferative disorders of the endometrium may include hyperplasia, metaplasia, and dysplasia of the endometrium.

In some embodiments, a compound of the present disclosure may be used to treat breast cancer, ovarian cancer, gastrointestinal cancer, lung cancer, colon cancer, endometrial cancer, or thyroid cancer.

In some embodiments, a compound of the present disclosure may be used to treat non-small-cell lung cancer (NSCLC) or EGFR/ALK/ROS1 triple-negative NSCLC.

The compounds of the present disclosure and their pharmaceutically acceptable salts and stereoisomers may be administered to a patient, e.g., a cancer patient, as a monotherapy or by way of combination therapy. Therapy may be "front/first-line", i.e., as an initial treatment in patients who have undergone no prior anti-cancer treatment regimens, either alone or in combination with other treatments; or "second-line", as a treatment in patients who have undergone a prior anti-cancer treatment regimen, either alone or in combination with other treatments; or as "third-line", "fourth-line", etc. treatments, either alone or in combination with other treatments. Therapy may also be given to patients who have had previous treatments which have been unsuccessful, or partially successful but who became non-responsive or intolerant to the particular treatment. Therapy may also be given as an adjuvant treatment, i.e., to prevent reoccurrence of cancer in patients with no currently detectable disease or after surgical removal of a tumor. Thus, in some embodiments, the compound may be administered to a patient who has received prior therapy, such as chemotherapy, radioimmunotherapy, surgical therapy, immunotherapy, radiation therapy, targeted therapy or any combination thereof.

The methods of the present disclosure may entail administration of an inventive compound or a pharmaceutical composition thereof to the patient in a single dose or in multiple doses (e.g., 1, 2, 3, 4, 5, 6, 7, 8, 10, 15, 20, or more doses). For example, the frequency of administration may range from once a day up to about once every eight weeks. In some embodiments, the frequency of administration ranges from about once a day for 1, 2, 3, 4, 5, or 6 weeks, and in other embodiments entails at least one 28-day cycle which includes daily administration for 3 weeks (21 days) followed by a 7-day off period. In other embodiments, the compound may be dosed twice a day (BID) over the course of two and a half days (for a total of 5 doses) or once a day (QD) over the course of two days (for a total of 2 doses). In other embodiments, the compound may be dosed once a day (QD) over the course of five days.

Combination Therapy

The compounds of the present disclosure and their pharmaceutically acceptable salts or stereoisomers may be used in combination or concurrently with at least one other active agent e.g., anti-cancer agent or regimen, in treating diseases and disorders. The terms "in combination" and "concurrently" in this context mean that the agents are co-administered, which includes substantially contemporaneous administration, by way of the same or separate dosage forms, and by the same or different modes of administration, or sequentially, e.g., as part of the same treatment regimen, or by way of successive treatment regimens. Thus, if given sequentially, at the onset of administration of the second agent, the first of the two agents is in some cases still detectable at effective concentrations at the site of treatment. The sequence and time interval may be determined such that they can act together (e.g., synergistically to provide an increased benefit than if they were administered otherwise). For example, the agents may be administered at the same time or sequentially in any order at different points in time; however, if not administered at the same time, they may be administered sufficiently close in time so as to provide the desired therapeutic effect, which may be in a synergistic fashion. Thus, the terms are not limited to the administration of the active agents at exactly the same time.

In some embodiments, the treatment regimen may include administration of a compound of the present disclosure or a pharmaceutically acceptable salt or stereoisomer thereof in combination with one or more additional therapeutic agents known for use in treating the disease or disorder (e.g., cancer). The dosage of the additional anticancer therapeutic may be the same or even lower than known or recommended doses. See, Hardman of al., eds., *Goodman & Gilman's The Pharmacological Basis Of Basis Of Therapeutics,* 10th ed., McGraw-Hill, New York, 2001; *Physician's Desk Reference* 60th ed., 2006. For example, anti-cancer agents that may be used in combination with the inventive compounds are known in the art. See, e.g., U.S. Pat. No. 9,101,622 (Section 5.2 thereof) and U.S. Pat. No. 9,345,705 82 (Columns 12-18 thereof). Representative examples of additional anti-cancer agents and treatment regimens include radiation therapy, chemotherapeutics (e.g., mitotic inhibitors, angiogenesis inhibitors, anti-hormones, autophagy inhibitors, alkylating agents, intercalating antibiotics, growth factor inhibitors, anti-androgens, signal transduction pathway inhibitors, anti-microtubule agents, platinum coordination complexes, HDAC inhibitors, proteasome inhibitors, and topoisomerase inhibitors), immune-modulators, therapeutic antibodies (e.g., mono-specific and bispecific antibodies) and CAR-T therapy.

In some embodiments, the compound provided herein and the additional anticancer therapeutic agent may be administered less than 5 minutes apart, less than 30 minutes apart, less than 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart. 60 hours to 72 hours apart, 72 hours to 84 hours apart, 84 hours to 96 hours apart, or 96 hours to 120 hours part. The two or more anticancer therapeutics may be administered within the same patient visit.

In some embodiments, the compound of the present disclosure and the additional therapeutic agent (e.g., an anti-cancer therapeutic) are cyclically administered. By way of example in the context of cancer treatment, cycling therapy involves the administration of one anticancer therapeutic for a period of time, followed by the administration of a second anti-cancer therapeutic for a period of time and repeating this sequential administration, i.e., the cycle, in order to reduce the development of resistance to one or both of the anticancer therapeutics, to avoid or reduce the side effects of one or both of the anticancer therapeutics, and/or to improve the efficacy of the therapies. In one example, cycling therapy involves the administration of a first anti-cancer therapeutic for a period of time, followed by the administration of a second anticancer therapeutic for a period of time, optionally, followed by the administration of a third anticancer therapeutic for a period of time and so forth, and repeating this sequential administration, i.e., the cycle in order to reduce the development of resistance to one of the anticancer therapeutics, to avoid or reduce the side effects of one of the anticancer therapeutics, and/or to improve the efficacy of the anticancer therapeutics.

In some embodiments, and depending on the particular cancer being treated, the compound of the present disclosure may be used in combination with at least one other anti-cancer agents such as Paclitaxel (e.g., ovarian cancer, breast cancer, lung cancer, Kaposi sarcoma, cervical cancer, and pancreatic cancer), Topotecan (e.g., ovarian cancer and lung cancer), Irinotecan (e.g., colon cancer, and small cell lung cancer), Etoposide (e.g., testicular cancer, lung cancer, lymphomas, and non-lymphocytic leukemia), Vincristine (e.g., leukemia), Leucovorin (e.g., colon cancer), Altretamine (e.g., ovarian cancer), Daunorubicin (e.g., acute myeloid leukemia (AML), acute lymphocytic leukemia (ALL), chronic myelogenous leukemia (CML), and Kaposi's sarcoma), Trastuzumab (e.g., breast cancer, stomach cancer, and esophageal cancer), Rituximab (e.g., non-Hodgkin's lymphoma), Cetuximab (e.g., colorectal cancer, metastatic non-small cell lung cancer and head and neck cancer), Pertuzumab (e.g., metastatic HER2-positive breast cancer), Alemtuzumab (e.g., chronic lymphocytic leukemia (CLL), cutaneous T-cell lymphoma (CTCL) and T-cell lymphoma), Panitumumab (e.g., colon and rectum cancer), Tamoxifen (e.g., breast cancer), Fulvestrant (e.g., breast cancer), Letrazole (e.g., breast cancer), Exemestane (e.g., breast cancer), Azacytidine (e.g., myelodysplastic syndromes), Mitomycin C (e.g., gastro-intestinal cancers, anal cancers, and breast cancers), Dactinomycin (e.g., Wilms tumor, rhabdomyosarcoma, Ewing's sarcoma, trophoblastic neoplasm, testicular cancer, and ovarian cancer), Erlotinib (e.g., non-small cell lung cancer and pancreatic cancer), Sorafenib (e.g., kidney cancer and liver cancer). Temsirolimus (e.g., kidney cancer), Bortezomib (e.g., multiple myeloma and mantle cell lymphoma), Pegaspargase acute lymphoblastic leukemia), Cabometyx (e.g., hepatocellular carcinoma, medullary thyroid cancer, and renal cell carcinoma). Keytruda (e.g., cervical cancer, gastric cancer, hepatocellular carcinoma, Hodgkin's lymphoma, melanoma, Merkel cell carcinoma, non-small cell lung cancer, urothelial carcinoma, and squamous cell carcinoma of the head and neck), Nivolumab (e.g., colorectal cancer, hepatocellular carcinoma, melanoma, non-small cell lung cancer, renal cell carcinoma, small cell lung cancer, and urothelial carcinoma), and Regorafenib (e.g., colorectal cancer, gastrointestinal stromal tumor, and hepatocellular carcinoma).

Pharmaceutical Kits

The present compositions may be assembled into kits or pharmaceutical systems. Kits or pharmaceutical systems according to this aspect of the present disclosure include a carrier or package such as a box, carton, tube or the like, having in close confinement therein one or more containers, such as vials, tubes, ampoules, or bottles, which contain a compound of the present disclosure or a pharmaceutical composition which contains the compound and a pharmaceutically acceptable carrier wherein the compound and the carrier may be disposed in the same or separate containers. The kits or pharmaceutical systems of the present disclosure may also include printed instructions for using the compounds and compositions.

These and other aspects of the present disclosure will be further appreciated upon consideration of the following Examples, which are intended to illustrate certain particular embodiments but are not intended to limit its scope, as defined by the claims.

EXAMPLES

Example 1: Synthesis of (R)—N-(4-([1,2,4]triazolo[1,5-a]pyridin-7-yloxy)-2,3-dimethylphenyl-1-(1-acryloylpiperidin-3-yl)-4-amino-1H-pyrazolo[3,4-d]pyrimidine-3-carboxamide (1)

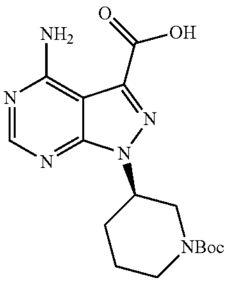

1

+

-continued

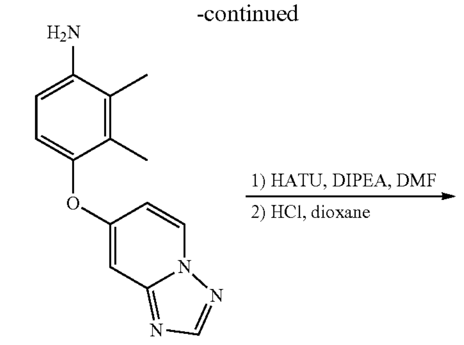

2

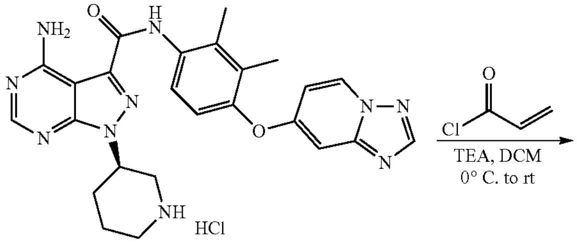

3

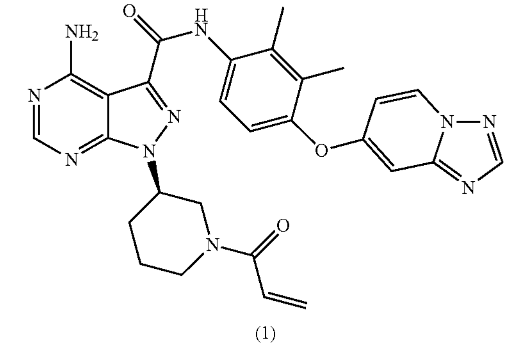

(1)

(R)—N-(4-([1,2,4]triazolo[1,5-a]pyridin-7-yloxy)-2,3-dimethylphenyl)-4-amino-1-(piperidin-3-yl)-1H-pyrazolo[3,4-d]pyrimidine-3-carboxamide hydrochloride (3). To a solution of acid 1 (150 mg, 0.414 mmol) (PBLJ7889 from Pharmablock) in DMF (4 was added hexafluorophosphate azabenzotriazole tetramethyl uranium (HATU, 189 mg, 0.497 mmol) and N,N-Diisopropylethylamine (DIPEA, 144 μL, 0.828 mmol), Aniline 2 (116 mg, 0.455 mmol) was then added and stirred at rt for 3 h. The reaction mixture was extracted with $EtOA_c$, washed with $H_2O$ 3×, brine, dried over $Na_2SO_3$, filtered, and concentrated by rotary evaporation. The crude residue was dissolved in 4 M HCl in dioxane (3 mL) and stirred for 1 h. The reaction mixture was concentrated to furnish crude intermediate amine 3 as a light orange solid.

(R)—N-(4-([1,2,4]triazolo[1,5-a]pyridin-7-yloxy)-2,3-dimethylphenyl)-1-(1-acryloylpiperidin-3-yl)-4-amino-1H-pyrazolo[3,4-d]pyrimidine-3-carboxamide (1). To a solution of intermediate amine 3 (200 mg, 0.374 mmol) in $CH_2Cl_2$ (3 mL, 0.12 M) at 0° C. were added triethylamine ($Et_3N$, 160 μL, 1.12 mmol) and acryloyl chloride (45 μL, 0.561 mmol). After stirring for 15 min at 0° C., the reaction mixture was warmed to rt, concentrated by rotary evaporation, and purified by preparative HPLC to obtain compound (1) as a white solid (61 mg, 14% over 3 steps from 1).

$^1H$ NMR (500 MHz, DMSO-$d_6$) δ 10.38-10.09 (m, 1H), 8.95 (d, J=7.5 Hz, 1H), 8.56 (s, 1H), 8.38 (s, 1H), 8.28 (s,

1H), 8.10 (s, 1H), 7.39 (d, J=8.4 Hz, 1H), 7.10 (d, J=8.6 Hz, 1H), 7.03 (dd, J=7.5, 2.7 Hz, 1H), 6.92-6.66 (m, 2H), 6.16-6.06 (m, 1H), 5.74-5.59 (m, 1H), 4.85-4.68 (m, 1H), 4.62-4.24 (m, 1H), 4.23-4.01 (m, 1H), 3.88-3.36 (m, 1H), 3.27-3.01 (m, 1H), 2.42-2.27 (m, 1H), 2.23 (s, 3H), 2.23-2.17 (m, 1H), 2.15 (s, 3H), 2.03-1.96 (m, 1H), 1.69-1.54 (m, 1H). LC-MS m/z: (pos) 553.55 ($[M+H]^+$).

Example 2: Synthesis of (R)—N-(4-([1,2,4]triazolo[1,5-a]pyridin-7-yloxy)-3-methylphenyl)-1-(1-acryloylpiperidin-3-yl)-4-amino-1H-pyrazolo[3,4-]pyrimidine-3-carboxamide (2)

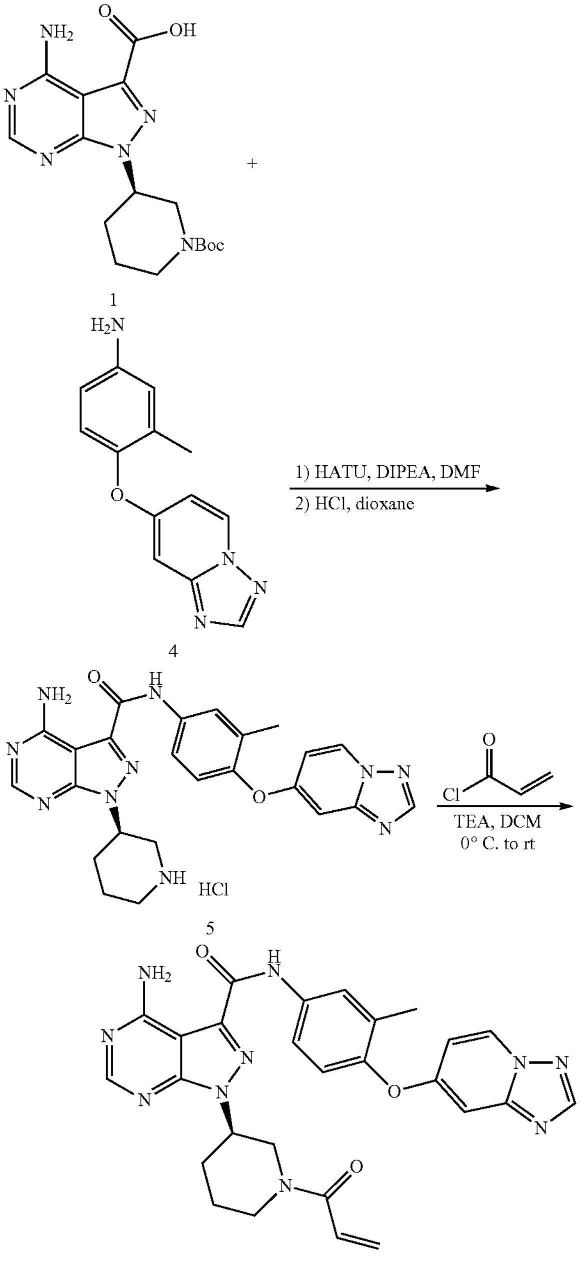

1

4

5

(2)

(R)—N-(4-([1,2,4]triazolo[1,5-a]pyridin-7-yloxy)-3-methylphenyl)-4-amino-1-(piperidin-3-yl)-1H-pyrazolo[3,4-d]pyrimidine-3-carboxamide hydrochloride (5). To a solution of acid 1 (120 mg, 0.331 mmol) in DMF (3 mL) was added HATU (151 mg, 0.397 mmol) and DIPEA (115 μL, 0.662 mmol). Aniline 4 (88 mg, 0.364 mmol) was then added and stirred at rt for 3 h. The reaction mixture was extracted with EtOAc, washed with $H_2O$ 3×, brine, dried over $Na_2SO_3$, filtered, and concentrated by rotary evaporation. The crude residue was dissolved in 4 M HCl in dioxane (3 mL) and stirred for 1 h. The reaction mixture was concentrated to furnish crude intermediate amine 5 as a light orange solid.

(R)—N-(4-([1,2,4]triazolo[1,5-a]pyridin-7-yloxy)-3-methylphenyl)-1-(1-acryloylpiperidin-3-yl)-4-amino-1H-pyrazolo[3,4-d]pyrimidine-3-carboxamide (2). To a solution of intermediate amine 5 (160 mg, 0.331 mmol) in $CH_2Cl_2$ (3 mL, 0.11 M) at 0° C. were added triethylamine ($Et_3N$, 140 μL, 0.99 mmol) and acryloyl chloride (40 μL, 0.497 mmol). After stirring for 15 min at 0° C., the reaction mixture was warmed to rt, concentrated by rotary evaporation, and purified by preparative HPLC to obtain (2) as a white solid (59 mg, 33% over 3 steps from 1).

$^1$H NMR (500 MHz, DMSO-$d_6$) δ 10.49-10.25 (m, 1H), 8.94 (d, J=7.5 Hz, 1H), 8.49 (s, 1H), 8.38 (s, 1H), 8.29 (s, 1H), 8.17 (s, 1H), 7.91 (s, 1H), 7.80 (d, J=8.5 Hz, 1H), 7.22 (d, J=8.5 Hz, 1H), 7.02 (dd, J=7.5, 2.6 Hz, 1H), 6.93-6.73 (m, 2H), 6.19-6.05 (m, 1H), 5.75-5.60 (m, 1H), 4.90-4.49 (m, 2H), 4.33-4.13 (m, 1H), 4.11-3.80 (m, 1H), 151-3.33 (m, 1H), 3.30-3.07 (m, 1H), 2.46-2.26 (m, 1H), 2.20 (s, 3H), 2.02-1.85 (m, 1H), 1.71-1.52 (m, 1H). LC-MS m/z: (pos) 539.57 ($[M+H]^+$).

Example 3: Synthesis of (R)—N-(4-([1,2,4]triazolo[1,5-a]pyridin-7-yloxy)-3-chlorophenyl)-1-(1-acryloylpiperidin-3-yl)-4-amino-1H-pyrazolo[3,4-d]pyrimidine-3-carboxamide

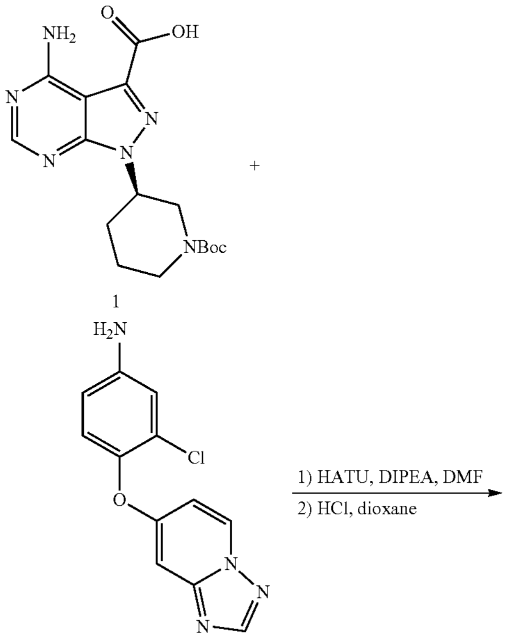

1

6

-continued

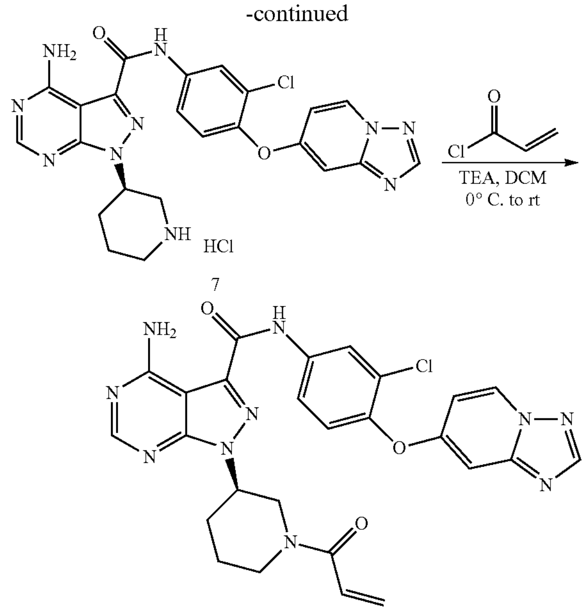

7

(3)

(R)—N-(4-([1,2,4]triazolo[1,5-a]pyridin-7-yloxy)-3-chlorophenyl)-4-amino-1-(piperidin-3-yl)-1H-pyrazolo[3,4-d]pyrimidine-3-carboxamide hydrochloride (7). To a solution of acid 1 (150 mg, 0.414 mmol) in DMF (4 mL) was added HATU (189 mg, 0.497 mmol) and DIPEA (144 μL, 0.828 mmol). Aniline 6 (119 mg, 0.455 mmol) was then added and stirred at rt for 3 h. The reaction mixture was extracted with EtOAc, washed with $H_2O$ 3×, brine, dried over $Na_2SO_3$, filtered, and concentrated by rotary evaporation. The crude residue was dissolved in 4 M HCl in dioxane (3 mL) and stirred for 1 h. The reaction mixture was concentrated to furnish crude intermediate amine 7 as a light orange solid.

(R)—N-(4-([1,2,4]triazolo[1,5-a]pyridin-7-yloxy)-3-chlorophenyl)-1-(1-acryloylpiperidin-3-yl)-4-amino-1H-pyrazolo[3,4-d]pyrimidine-3-carboxamide (3). To a solution of intermediate amine 7 (200 mg, 0.396 mmol) in $CH_2Cl_2$ (3 mL, 0.13 M) at 0° C. were added triethylamine ($Et_3N$, 173 μL, 1.24 mmol) and acryloyl chloride (50 μL, 0.62 mmol). After stirring for 15 min at 0° C., the reaction mixture was warmed to rt, concentrated by rotary evaporation, and purified by preparative HPLC to obtain (3) as a white solid (39 mg, 17% over 3 steps from 1).

$^1H$ NMR (500 MHz, DMSO-$d_6$) δ 10.76-10.47 (m, 1H), 8.97 (d, J=7.5 Hz, 1H), 8.50-8.34 (m, 2H), 8.30 (s, 1H), 8.25 (s, 1H), 8.20 (s, 1H), 7.96 (dd, J=8.9, 2.3 Hz, 1H), 7.48 (d, J 8.7 Hz, 1H), 7.07 (dd, J=7.5, 2.6 Hz, 1H), 6.96 (d, J=2.4 Hz, 1H), 6.93-6.70 (m, 1H), 6.13 (t, 1H), 5.68 (dd, 1H), 4.86-4.71 (m, 1H), 4.62-4.25 (m, 1H), 4.25-4.03 (m, 1H), 3.91-3.39 (m, 1H), 3.27-3.01 (m, 1H), 2.46-2.27 (m, 1H), 2.26-2.12 (m, 2H), 2.01-1.85 (m, 1H), 1.74-1.53 (m, 1H). LC-MS m/z: (pos) 559.51 ($[M+H]^+$).

Example 4: HER2 Inhibitory Activity

The $IC_{50}$ values of the compounds provided herein were measured against kinases in Ba/F3 cells. Tables 1 and 2 summarize the data for the compounds disclosed herein in comparison to TAS0728,

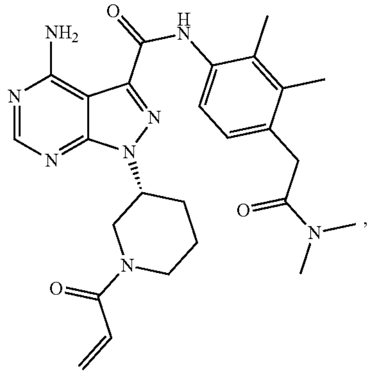

a commercially available HER2 inhibitor.

Activities of representative compounds of the present application in inhibiting EGFR and HER2 were tested by MTS assay (Abcam®) for Ba/F3 cells. For assays with Ba/F3 cells, 3000 cells were seeded for per well in 96-well plates and were exposed to the indicated compounds with a concentration of 3.3 to 10 μM for 72 hours. The data in Tables 1 and 2 show that the inventive compounds, particularly compounds 1-3, are highly potent and selective inhibitors of Her2 and Her2 20 insertion mutants vs EGFR wt and EGFR mutants.

TABLE 1

$IC_{50}$ (μM) Ba/F3 data for Compounds 1-3

| Cell Line | TAS0728 | Compound 1 | Compound 2 | Compound 3 |
|---|---|---|---|---|
| EFGR WT | 0.9208 | 1.379 | 3.274 | 2.113 |
| EFGR SVD | 4.477 | 2.619 | 3.984 | 2.615 |
| EFGR ASV | 3.82 | 1.815 | 2.238 | 1.46 |
| HER2 WT | 0.1638 | 0.1108 | 0.1926 | 0.09811 |
| HER2 YVMA | 0.206 | 0.0322 | 0.05588 | 0.04554 |
| HER2 GSP | 0.06432 | 0.05666 | 0.09581 | 0.0786 |

TABLE 2

$IC_{50}$ (μM) Ba/F3 data for Compounds 4-11

| Cell Line | Cmpd 4 | Cmpd 5 | Cmpd 6 | Cmpd 7 | Cmpd 8 | Cmpd 9 | Cmpd 10 | Cmpd 11 |
|---|---|---|---|---|---|---|---|---|
| EFGR WT | 7.162 | 8.959 | 9.422 | 8.79 | 9.455 | 7.923 | 138.4 | >10 |
| EFGR SVD | 6.045 | 7.623 | 7.84 | 7.721 | 6.753 | 5.587 | 18.39 | — |
| EFGR ASV | 4.534 | 5.717 | 6.806 | 6.024 | 4.27 | 1.98 | — | — |

TABLE 2-continued

| IC$_{50}$ (μM) Ba/F3 data for Compounds 4-11 | | | | | | | | |
|---|---|---|---|---|---|---|---|---|
| Cell Line | Cmpd 4 | Cmpd 5 | Cmpd 6 | Cmpd 7 | Cmpd 8 | Cmpd 9 | Cmpd 10 | Cmpd 11 |
| HER2 WT | 3.846 | 4.078 | 5.793 | 6.296 | 3.237 | 2.625 | 3.43 | 5.96 |
| HER2 YVMA | 3.156 | 4.474 | 7.557 | 8.837 | 1.846 | 1.381 | 0.58 | 1.33 |
| HER2 GSP | 1.44 | 2.394 | 5.641 | 6.289 | 1.387 | 1.294 | — | — |

All patent publications and non-patent publications are indicative of the level of skill of those skilled in the art to which this disclosure pertains. All these publications are herein incorporated by reference to the same extent as if each individual publication were specifically and individually indicated as being incorporated by reference.

Although the disclosure herein has been described with reference to particular embodiments, it is to be understood that these embodiments are merely illustrative of the principles and applications of the present disclosure. It is therefore to be understood that numerous modifications may be made to the illustrative embodiments and that other arrangements may be devised without departing from the spirit and scope of the present disclosure as defined by the appended claims.

The invention claimed is:

1. A compound having a structure represented by Formula I:

(I)

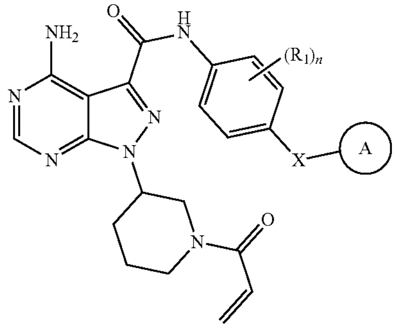

or a pharmaceutically acceptable salt or stereoisomer thereof, wherein:

X is absent, —$CH_2$—, —O—, or C(O)—;

A is an unsaturated fused-heterobicyclyl having 5- or 6-membered rings containing 1-4 N atoms, or an unsaturated 5-membered heterocyclyl containing 1-3 N atoms;

each $R_1$ is independently $C_1$-$C_6$ alkyl or halo; and n is 0, 1, or 2.

2. A compound of claim 1 having a structure represented by formula Ia, Ib, Ic, Id, Ie, If, Ig, or Ih:

(Ia)

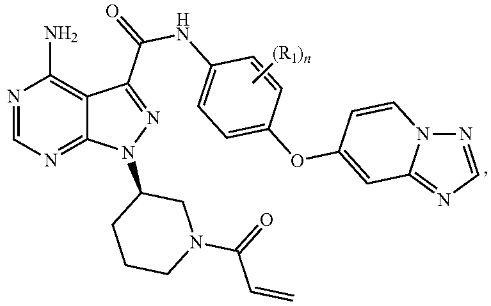

, (Ib)

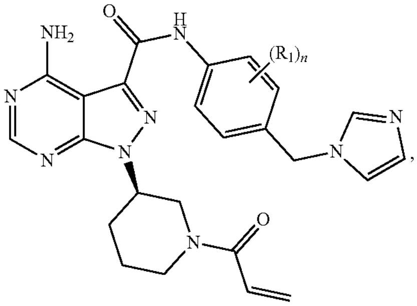

, (Ic)

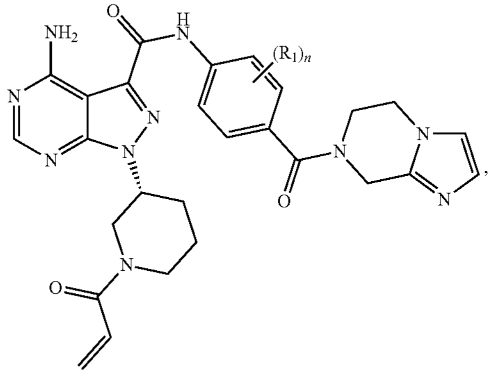

,

-continued
(Id)
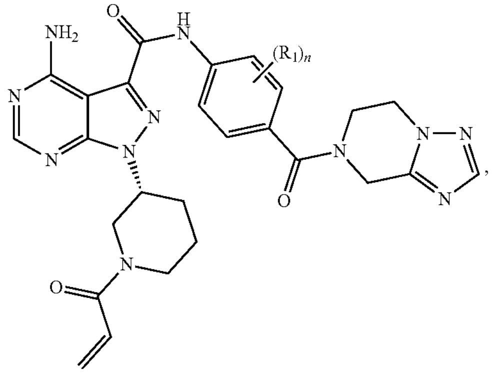
(Ie)
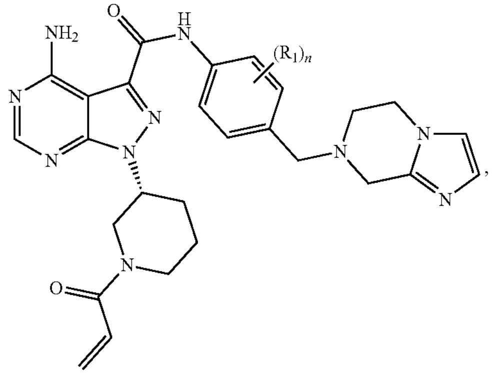
(If)
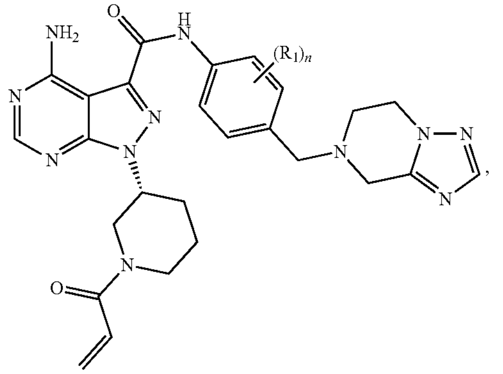
(Ig)
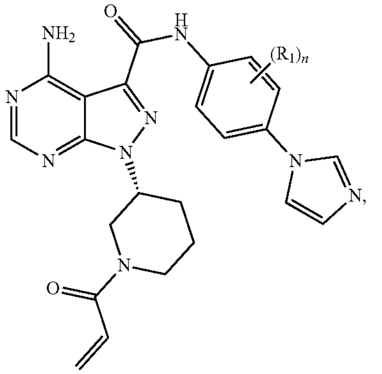
or
-continued
(Ih)
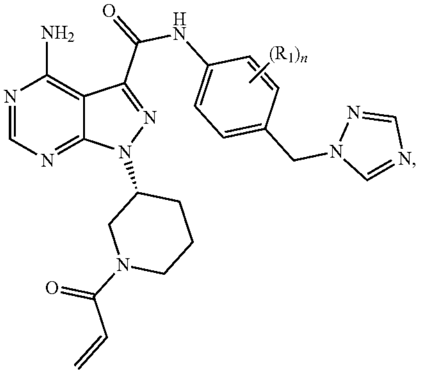
or a pharmaceutically acceptable salt or stereoisomer thereof.
3. The compound of claim 1, wherein each $R_1$ is independently methyl or chloro.
4. The compound of claim 1, wherein n is 1 or 2.
5. The compound of claim 1, which is selected from the group consisting of:
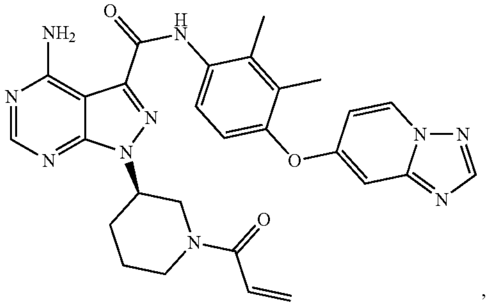
,
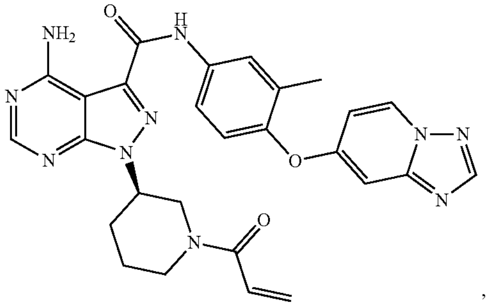
,
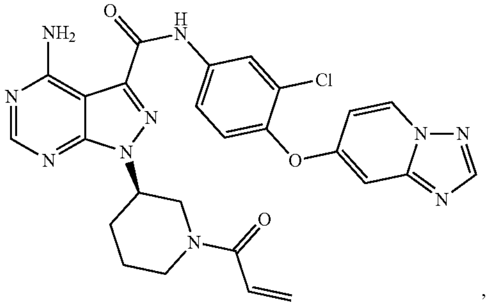
, -continued
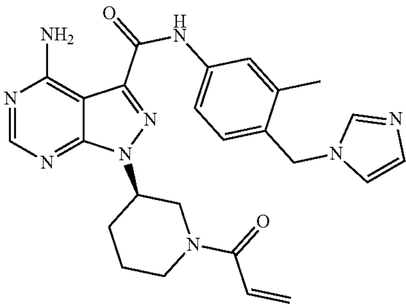
,
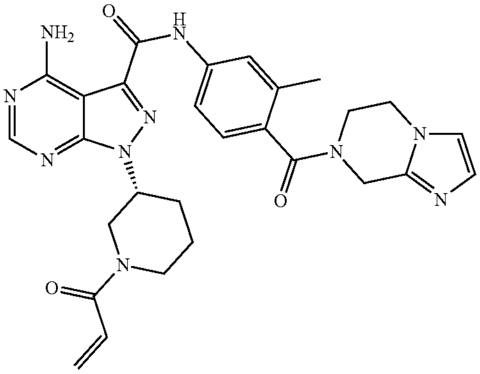
,
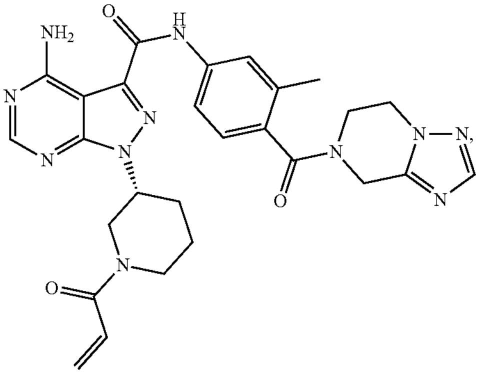
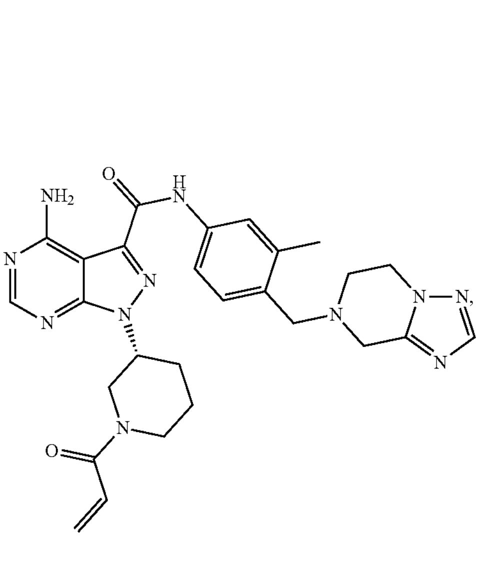
-continued
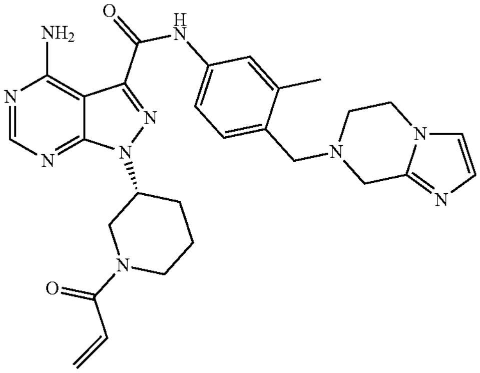
,
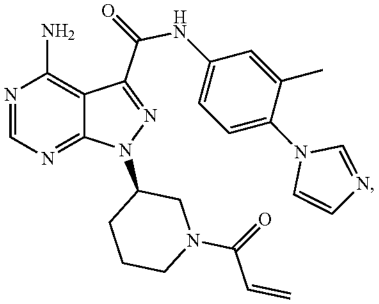
and
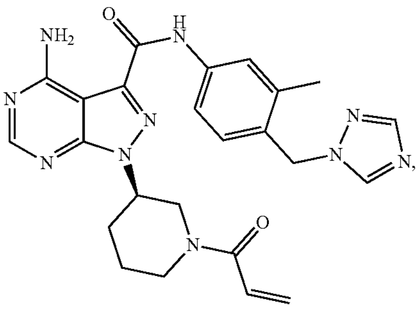
or a pharmaceutically acceptable salt or stereoisomer thereof.
6. A pharmaceutical composition, comprising a therapeutically effective amount of the compound or pharmaceutically acceptable salt or stereoisomer thereof of claim 1, and a pharmaceutically acceptable carrier.

7. The compound of claim 1 having a structure represented by formula Ia:
(Ia)
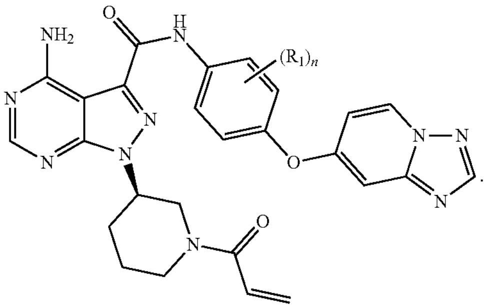
8. The compound of claim 7 selected from the group consisting of compounds:
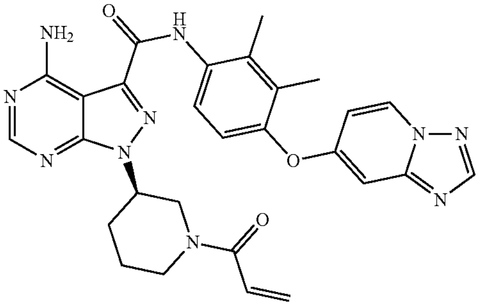
,
-continued
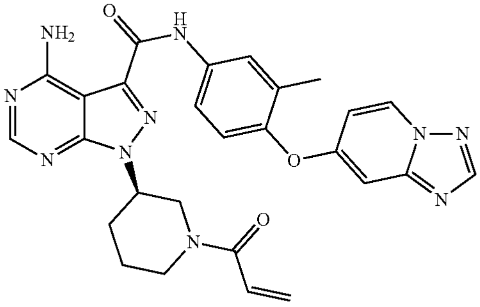
, and
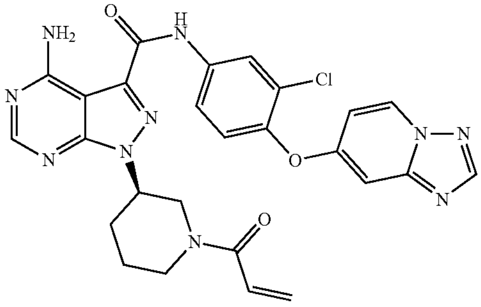
.
* * * * *